US008338643B2

(12) United States Patent
Takeoka et al.

(10) Patent No.: US 8,338,643 B2
(45) Date of Patent: Dec. 25, 2012

(54) REAGENT FOR INTRODUCTION OF PROTEIN OR GENE

(75) Inventors: Shinji Takeoka, Tokyo (JP); Naoya Takeda, Tokyo (JP); Hitoshi Kurumizaka, Tokyo (JP); Isao Sakane, Tokyo (JP); Namiko Ikegaya, Tokyo (JP); Yosuke Obata, Tokyo (JP); Syunsuke Saito, Kawasaki (JP)

(73) Assignee: Waseda University, Tokyo (JP)

( * ) Notice: Subject to any disclaimer, the term of this patent is extended or adjusted under 35 U.S.C. 154(b) by 652 days.

(21) Appl. No.: 12/312,648

(22) PCT Filed: Nov. 26, 2007

(86) PCT No.: PCT/JP2007/073266
§ 371 (c)(1),
(2), (4) Date: Jul. 7, 2009

(87) PCT Pub. No.: WO2008/062911
PCT Pub. Date: May 29, 2008

(65) Prior Publication Data
US 2010/0291672 A1    Nov. 18, 2010

(30) Foreign Application Priority Data

Nov. 24, 2006  (JP) .................................. 2006-317841

(51) Int. Cl.
| | |
|---|---|
| C07C 251/00 | (2006.01) |
| C07C 233/00 | (2006.01) |
| C07C 253/00 | (2006.01) |
| C07C 237/00 | (2006.01) |
| C07C 239/00 | (2006.01) |
| C07C 321/00 | (2006.01) |
| C07C 323/00 | (2006.01) |
| C07C 381/00 | (2006.01) |

(52) U.S. Cl. ............................ 562/624; 564/123; 568/22
(58) Field of Classification Search .................. 562/624; 564/123; 568/22
See application file for complete search history.

(56) References Cited

FOREIGN PATENT DOCUMENTS
JP    11-504631 A    4/1999
(Continued)

OTHER PUBLICATIONS

Bhattacharya et al., "Recent Advances in Lipid Molecular Design," Current Opinion in Chemical Biology, 2005, vol. 9, pp. 647-655.

(Continued)

*Primary Examiner* — Benjamin Packard
(74) *Attorney, Agent, or Firm* — Birch Stewart Kolasch & Birch, LLP

(57) ABSTRACT

The present invention provides a reagent for introducing a protein or gene into a cell. The reagent of the present invention is, for example, a reagent for introducing a protein or gene into a cell, which comprises a composition comprising a cationic amino acid type lipid represented by the following formula (I)-1:

(I)-1

$$H_2N-\overset{\displaystyle\phantom{|}}{\underset{\displaystyle\phantom{|}}{\bigg\langle}}-L-M^1-\overset{O}{\underset{\|}{C}}-\overset{H}{\underset{|}{N}}-\overset{\displaystyle\phantom{|}}{\underset{(CH_2)_2-\underset{\|}{\overset{O}{C}}-O-(CH_2)_{m2}-CH_3}{\overset{\overset{O}{\|}}{C}-O-(CH_2)_{m1}-CH_3}}$$

$$H_2N$$

(wherein in formula (I)-1: L is a single bond, —CONH—, or —S—S—; $M^1$ is —$(CH_2)_k$— or —$(CH_2CH_2O)_k$— (wherein k is an integer between 0 and 14); and m1 and m2 are each independently an integer between 11 and 21 (in this regard, when providing a reagent for introducing a gene into a cell, the case where both m1 and m2 are 15 is excluded)).

23 Claims, 11 Drawing Sheets
(5 of 11 Drawing Sheet(s) Filed in Color)

Confocal microscopic images of COS-1 cells transfected with liposomes encapsulating Dmcl

FOREIGN PATENT DOCUMENTS

| | | |
|---|---|---|
| WO | WO-96/34109 A | 10/1996 |
| WO | WO-2006/118327 A1 | 11/2006 |

OTHER PUBLICATIONS

European Search Report issued Dec. 14, 2010, in European Patent Application No. 07849971.

Sebyakin et al., "pH-Sensitive Cationic Lipopeptides for the Design of Drug-Delivery Systems," Russian Journal of Bioorganic Chemistry, 2006, vol. 32, No. 5, pp. 407-412.

D. J. Stephens et al., "The many ways to cross the plasma membrane", Proc. Natl. Acad. Sci. USA, 2001, vol. 98, No. 8 p. 4295-4298.

M.A. Sells et al., Delivery of protein into cells using polycationic liposomes, Biotechniques, 1995, vol. 19, No. 1, p. 72-76, 78.

H.S. Kim et al., "In vitro and in vivo gene-transferring characteristics of novel cationic lipids, DMKD (O, O'-dimyristyl-N-lysyl asparate) and DMKE (O, O'-dimyristyl-N-lysyl glutamate)", J. Controlled Release, Oct. 10, 2006, vol. 115, No. 2, p. 234-241.

H.S. Kim et al., "Gene-Transferring efficiencies of novel diamino cationic lipids with varied hydrocarbon chains", Bioconjugate Chem. 2004, 15, p. 1095-1101.

L. Stamatatos et al., "Interactions of cationic lipid vesicles with negatively charged phospholipid vesicles and biological membranes", Biochemistry, 1988, 27, p. 3917-3925.

T. Kinebuchi et al., "Structural basis for octameric ring formation and DNA interaction of the human homologus-Pairing protein Dmcl", Molecular Cell, 2004, vol. 14, p. 363-374.

Confocal microscopic images of COS-1 cells transfected with liposomes encapsulating Dmc1 a: Dmc1-encapsulated liposome (cytoplasm, nucleus)
b: Comparison between Dmc1-encapsulated liposome and control (nucleus)

Confocal microscopic images of NIH-3T3 cells transfected
with liposomes encapsulating Dmc1

Confocal microscopic images of COS-1 cells transfected with
liposomes encapsulating rHSA Confocal microscopic images of COS-1 cells ((A) cationic; (B) zwitterionic; and (C) anionic)
(nucleus: blue; and liposome: red)

Confocal microscopic images in the presence of encapsulated TRITC-labeled rHSA liposome composed of (a) DOPC/chol/PEG, (b) DOPC/chol/Lys-Glu2$C_{16}$/PEG, and (c) DOPC/chol/Lys-$C_5$-Glu2$C_{16}$/PEG.

(a) Vesicle + pDNA
(b) pDNA-encapsulating liposome

REAGENT FOR INTRODUCTION OF PROTEIN OR GENE

TECHNICAL FIELD

The present invention relates to a reagent for introducing a protein or gene into a cell, which comprises a composition comprising a complex lipid having a cationic functional group derived from an amino acid.

BACKGROUND ART

Technologies for encapsulating a useful substance in a vesicle or liposome, which is formed of an artificial bilayer membrane, are actively studied in the fields of pharmaceutical drugs, cosmetics, foods, dyes and the like.

Widely used lipids for forming a membrane of a liposome include, for example, a mixed lipid of a membrane-forming lipid such as diacylphosphatidylcholine, cholesterol or the like and a negatively charged phospholipid such as diacylphosphatidylglycerol, diacylphosphatidylinositol, diacylphosphatidylserine or the like.

Recently, it has been studied to introduce a gene into a cell by forming a complex of the gene and an independent cationic lipid or a liposome containing the cationic lipid (Hong Sung Kim et al., Gene-transferring efficiencies of novel diamino cationic lipids with varied hydrocarbon chains. Bioconjugate Chem. 2004, 15, 1095). Most of existing cationic lipids for gene introduction, such as 1,2-dioleoyloxy-3-trimethylammonium propane (DOTAP), 3β-N-(N',N'-dimethyl-aminoethane)-carbamoyl cholesterol (DC-Chol), 1,2-dimyristyloxypropyl-3-dimethylhydroxyethyl ammonium (DMRIE), 2,3-dioleyloxy-N-[2(sperminecarboxamido)ethyl]-N,N-dimethyl-1-propanaminium trifluoroacetate (DOSPA), dioctadecyldimethylammonium chloride (DODAC), N-(2,3-dioleyloxy)propyl-N,N,N-trimethylammonium (DOTMA), didodecyldimethylammonium bromide (DDAB) and Lipofectamine, have quaternary amine for imparting positive charge to the hydrophilic portion of lipid component. Unlike gene introduction carriers using a cationic polymer such as polyethyleneimine, gene introduction systems using these cationic lipids do not have the proton sponge effect in which a complex with DNA leaves from an endosome. Therefore, existing cationic lipids for gene introduction are usually mixed with 1,2-dioleoyl-sn-glycero-3-phosphoethanolamine (DOPE), which is a membrane-fusogenic lipid. A cationic lipid has the action to concentrate and stabilize DNA, and DOPE promotes fusion with an endosome membrane, thereby releasing the cationic lipid-DNA complex to the outside of the endosome membrane. Thus, introduction of DNA which is concentrated and stabilized by the cationic lipid into the nucleus is accomplished (L. Stamatatos et al., Interactions of cationic lipid vesicles with negatively charged phospholipid vesicles and biological membranes. Biochemistry 1988, 27, 3917; Japanese National-phase PCT Laid-Open Patent Publication No. 11-504631).

However, it is not easy to synthesize the above-described cationic lipid for gene introduction because of its complicated chemical structure, and under present circumstances, such reagents for gene introduction are expensive. Moreover, lipids for gene introduction having quaternary amine tend to cause aggregation with serum component because the lipids are strongly cationic, and this may cause significant reduction in the gene introduction efficiency in the presence of serum. Furthermore, these cationic lipids strongly interact with phospholipid on the surface of cell membrane, and therefore cell cytotoxicity thereof is high.

Meanwhile, a carrier is also required in the case where a protein is introduced from the outside into a cell. As such carriers, lipid-based reagents (e.g., Profect P-1, BioPORTER, and SAINT-MIX), peptide-based reagents (e.g., Profect P-2, and Chariot), etc. are available. However, since most of these carriers are simply mixed with a protein to form a complex and it is added to a cell for use, it is often impossible to control the size of the complex. Further, particularly in the case of lipid-based carriers, the efficiency of introduction of a protein of interest is significantly reduced when serum protein is contained in a cell culture solution, and therefore it is required to make an experiment using a medium without containing serum. Moreover, when an excess amount of free lipid carrier is present, significant cell cytotoxicity may appear.

DISCLOSURE OF THE INVENTION

The purpose of the present invention is to provide a reagent for introducing a protein or gene, which can efficiently introduce the protein or gene into a cell and can be synthesized easily and inexpensively, and which has high biocompatibility (i.e., low toxicity).

The present inventors diligently made researches in order to solve the above-described problem, and found that, when a protein or gene is encapsulated in a molecular assembly such as a bilayer membrane vesicle constituted by a cationic amino acid type lipid and the obtained product is subjected to a test of introduction of the protein or gene into a cell, the protein or gene can be efficiently introduced into the cell. Thus, the present invention was achieved.

That is, the present invention provides a reagent for introducing a protein or gene into a cell, which comprises a composition comprising a cationic amino acid type lipid as described below. In addition, the present invention provides a kit for introducing a protein or gene into a cell, which comprises the reagent.

A cationic amino acid type lipid represented by general formula (I):

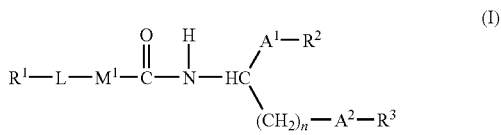

(wherein in formula (I): $R^1$ is a hydrocarbon group having a cationic functional group derived from an amino acid; $R^2$ and $R^3$ are each independently a chain hydrocarbon group; $A^1$ and $A^2$ are each independently a linkage group selected from the group consisting of —COO—, —CONH— and —NHCO—; L is a single bond, —CONH—, or —S—S—; $M^1$ is —$(CH_2)_k$— or —$(CH_2CH_2O)_k$— (wherein k is an integer between 0 and 14); and n is an integer between 1 and 4).

Examples of cationic functional groups include those selected from the group consisting of amino group, guanidino group, imidazole group and derivatives thereof.

In formula (I), examples of $R^1$ include a substance represented by formula (a):

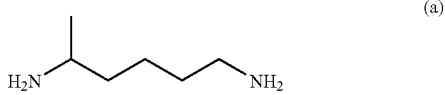

Further, in formula (I), it is preferred that both $A^1$ and $A^2$ are —COO—. Moreover, it is preferred that $R^2$ and $R^3$ are each independently a saturated or unsaturated chain hydrocarbon group including the main chain having 12 to 30 carbon atoms, which may have a substituent selected from the group consisting of alkyl group, alkenyl group, alkynyl group, isoprenoid group, carboxyl group, hydroxyl group, amino group and mercapto group. It is more preferred that $R^2$ and $R^3$ are each independently an alkyl chain having 12 to 22 carbon atoms, and preferably 14 to 18 carbon atoms. Further, in formula (I), n is preferably 2.

Furthermore, in the present invention, a cationic amino acid type lipid represented by formula (I)-1 can be used:

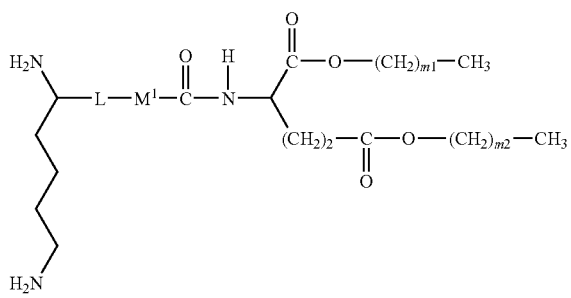

(I)-1

(wherein in formula (I)-1: L is a single bond, —CONH—, or —S—S—; $M^1$ is —$(CH_2)_k$— or —$(CH_2CH_2O)_k$— (k is an integer between 0 and 14 (preferably between 0 and 11)); and m1 and m2 are each independently an integer between 11 and 21 (in this regard, when providing a reagent for introducing a gene into a cell and a kit for introducing a gene into a cell comprising the reagent, the case where both m1 and m2 are 15 is excluded)).

Further, specific examples of the cationic amino acid type lipid represented by formula (I)-1 include a cationic amino acid type lipid represented by formula (I)-2:

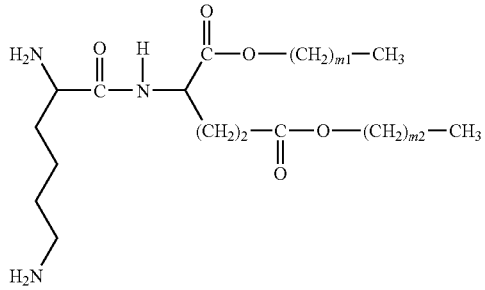

(I)-2

(wherein in formula (I)-2, m1 and m2 are the same as the case of formula (I)-1).

In the present invention, the composition comprising the cationic amino acid type lipid may include diacylphosphatidylcholine. In this case, one or two acyl chains of diacylphosphatidylcholine is preferably an oleoyl group. Specifically, the above-described composition may include 1,2-dioleoyl-sn-glycero-3-phosphatidylcholine (DOPC).

The above-described composition may further include cholesterol. Moreover, the composition may further include an amphipathic molecule to which a polyethylene glycol chain is bound.

The above-described composition may be in the form of a molecular assembly dispersed in an aqueous medium or in the form of a dry powder product. The molecular assembly forms a bilayer membrane vesicle structure, and an inner aqueous phase thereof includes a protein or gene. In the case of the dry powder product, when it is dispersed in an aqueous medium, it can form a bilayer membrane vesicle structure including a protein or gene. In this regard, examples of cells to be targeted for introduction of a protein or gene include plasma, serum, blood, and a cell cultured in a medium containing a part of components thereof.

The present invention may also be a cationic amino acid type lipid represented by general formula (I'):

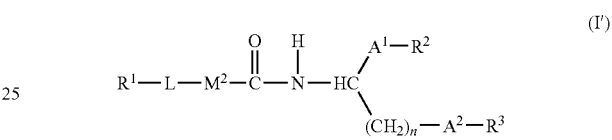

(I')

(wherein in formula (I'): $R^1$ is a hydrocarbon group having a cationic functional group derived from an amino acid; $R^2$ and $R^3$ are each independently a chain hydrocarbon group; $A^1$ and $A^2$ are each independently a linkage group selected from the group consisting of —COO—, —COO—, —CONH— and —NHCO—; L is a single bond, —CONH—, or —S—S—; $M^2$ is —$(CH_2)_{k'}$— or —$(CH_2CH_2O)_{k'}$— (wherein k' is an integer between 1 and 14); and n is an integer between 1 and 4).

$R^1$, $R^2$ and $R^3$ and $A^1$ and $A^2$ are the same as described above. Further, n is preferably 2.

The present invention may also be a cationic amino acid type lipid represented by the following formula (I)-3:

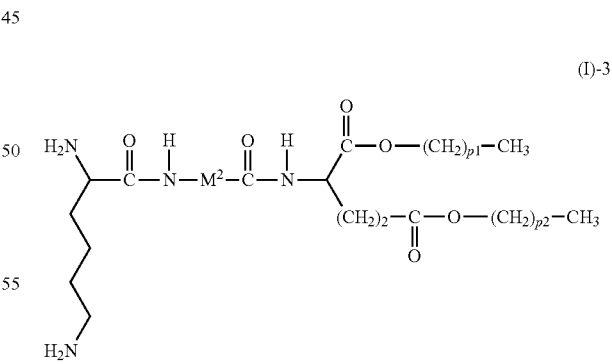

(I)-3

(wherein: $M^2$ is —$(CH_2)_{k'}$— or —$(CH_2CH_2O)_{k'}$— (k' is an integer between 1 and 14 (preferably between 1 and 11)); and p1 and p2 are each independently an integer between 11 and 21).

Specific examples of the cationic amino acid type lipid represented by formula (I)-3 include cationic amino acid type lipids represented by formulae (I)-4 and (I)-5:

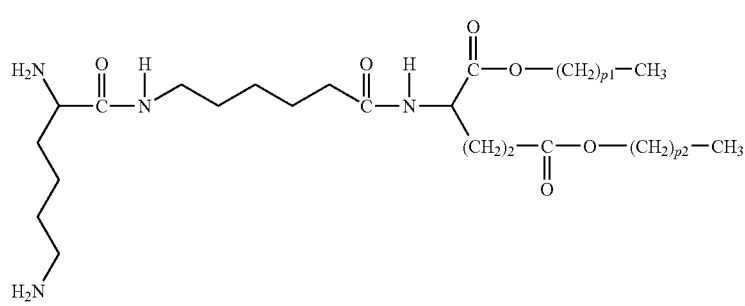

(I)-4

(wherein in formula (I)-4, p1 and p2 are the same as the case of formula (0-3).

BRIEF DESCRIPTION OF THE DRAWINGS

The patent or application file contains at least one drawing executed in color. Copies of this patent or patent application publication with color drawings will be provided by the office upon request and payment of the necessary fee.

BEST MODE FOR CARRYING OUT THE INVENTION

Figure 1:
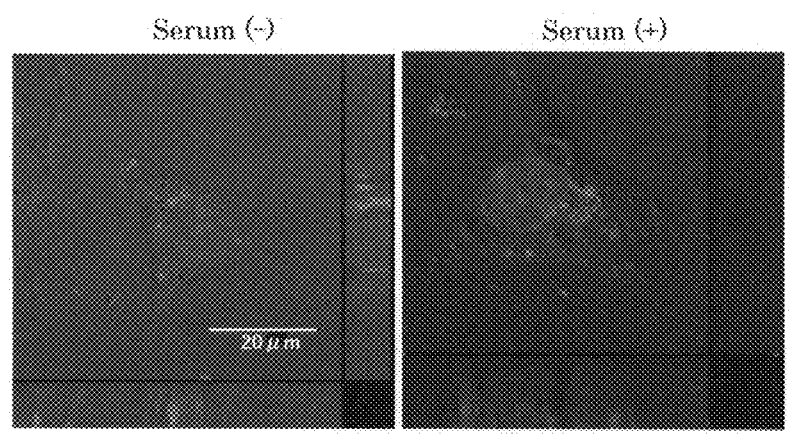
FIG. 1 shows confocal laser microscopic images of liposome/Dmc1 complexes introduced into COS-1 cells.

Hereinafter, the present invention will be described in detail. The scope of the present invention is not limited to the description. In addition to the following examples, the present invention can be suitably changed and then practiced within a range in which the effects of the present invention are not reduced.

Note that the entire specification of Japanese Patent Application No. 2006-317841, to which priority is claimed by the present application, is incorporated herein. In addition, all the publications such as prior art documents, laid-open publications, patents and other patent documents cited herein are incorporated herein by reference.

In the present invention, a molecular assembly, which has a complex lipid having a cationic functional group derived from an amino acid as a constituent, is utilized as a reagent for introducing a protein or gene.

The present inventors constructed a carrier system for a protein or gene using a liposome, in which a protein or gene is encapsulated in a liposome having a component composition exhibiting low adsorptive property to the cell surface and low cell cytotoxicity to stabilize a complex, and the particle size of the liposome is adjusted by the extrusion method. By encapsulating proteins or genes in liposomes to provide nanoparticles with a uniform particle size, the ability to be taken into a cell is improved, and it is possible to inhibit degradation of the encapsulated protein by protease in the cell and degradation of the encapsulated gene by nuclease.

Hereinafter, the cationic amino acid type lipid of the present invention and a composition comprising the same will be described in detail.

1. Cationic Amino Acid Type Lipid 1-1) Cationic Amino Acid Type Lipid

The cationic amino acid type lipid to be used in the present invention is characterized in that it is represented by general formula (I):

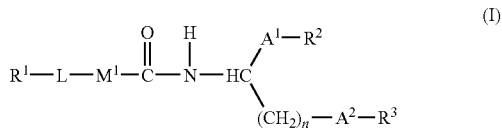

(I)

(wherein in formula (I): $R^1$ is a hydrocarbon group having a cationic functional group derived from an amino acid; $R^2$ and $R^3$ are each independently a chain hydrocarbon group; $A^1$ and $A^2$ are each independently a linkage group selected from the group consisting of —COO—, —COO—, —CONH— and —NHCO—; L is a single bond, —CONH—, or —S—S—; $M^1$ is —$(CH_2)_k$— or —$(CH_2CH_2O)_k$— (wherein k is an integer between 0 and 14); and n is an integer between 1 and 4).

In formula (I), $R^1$ is a hydrocarbon group having a cationic functional group derived from an amino acid. In this regard, the term "cationic functional group" refers to any group exhibiting a cationic property in an aqueous solution, and it is not particularly limited as long as it has the above-described property. Examples of the cationic functional group include amino group, guanidino group, imidazole group, and derivatives thereof. Examples of the "derivatives" include compounds obtained as a result of a hydrogen atom contained in an amino group, a guanidino group or an imidazole group being substituted with a substituent such as lower (for example, having 1 to 6 carbon atoms) alkyl group (methyl, ethyl, propyl, isopropyl, n-butyl, sec-butyl, etc.), aminoalkyl group (aminomethyl, aminoethyl, aminopropyl, aminobutyl, etc.) and corresponding oligoaminoalkyl group, hydroxyl group, hydroxyalkyl group (hydroxymethyl, hydroxyethyl, hydroxypropyl, etc.), oligooxyalkyl group (oligooxymethyl group, oligooxyethyl group, oligooxypropyl, etc.) or the like.

$R^1$ may have at least one cationic functional group, but preferably has two or more cationic functional groups. In particular, a compound having two or more cationic functional groups is preferred on the point that it can stably form a complex with a protein or a nucleic acid such as a DNA or an RNA, which is a polyanion. A compound having two or more cationic functional groups is also preferred on the point that it is stably linked to an area of a cell surface where negative charges are concentrated, which improves the intracellular migration capability. When the compound has two or more cationic functional groups, there is no specific limitation on the combination thereof.

Among the above-listed groups, $R^1$ is preferably a group represented by the following formula (a).

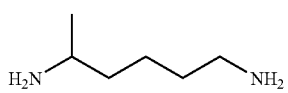

(a)

In formula (I), $R^2$ and $R^3$ are each independently a chain hydrocarbon group. There is no specific limitation on the "chain hydrocarbon group" as long as the chain hydrocarbon group is a hydrophobic group which can be introduced by covalent bond to the linkage group $A^1$ or $A^2$. The chain hydrocarbon group may be either of straight chain or branched chain, but is preferably a straight chain. The number of carbon atoms in the main chain of the chain hydrocarbon group is preferably 12 to 30, more preferably 12 to 22, and even more preferably 14 to 18. The chain hydrocarbon group may be saturated or unsaturated, but in the case where the chain hydrocarbon group has an unsaturated bond(s) such as a double bond or a triple bond, the number of the unsaturated bond(s) is preferably 1 to 4. The main chain of the chain hydrocarbon group is preferably an alkyl chain, an alkenyl chain or an alkynyl chain, and is more preferably an alkyl chain.

The chain hydrocarbon group may have a substituent selected from the group consisting of alkyl group, alkenyl group, alkynyl group, isoprenoid group, carboxyl group, hydroxyl group, amino group, and mercapto group. The alkyl group preferably has a carbon number of 1 to 6, and examples thereof include methyl group, ethyl group, propyl group, isopropyl group, n-butyl group, sec-butyl group, tert-butyl group, pentyl group, hexyl group and the like. The alkenyl group preferably has a carbon number of 1 to 6, and examples thereof include vinyl group, allyl group, propenyl group, isopropenyl group, 2-butenyl group and the like. The alkynyl group preferably has a carbon number of 1 to 6, and examples thereof include ethynyl group, propynyl group, butynyl group and the like.

Among the above-listed chain hydrocarbon groups, $R^2$ and $R^3$ are each preferably an alkyl chain having 12 to 22 carbon atoms which may optionally have a substituent.

In formula (I), $A^1$ and $A^2$ are each independently a linkage group selected from the group consisting of —COO—, —COO—, —CONH— and NHCO—. $A^1$ and $A^2$ may be any of these linkage groups with any combination with no specific limitation, but it is preferable that $A^1$ and $A^2$ are both —COO—.

In formula (I), n is an integer of 1 to 4. It is preferable that n is an integer of 1 to 4 because in such a case, the chain hydrocarbon group of the compound represented by formula (I) can be aligned in the bilayer membrane vertically with respect to the flat surface of the membrane. In addition, when n is an integer of 1 to 4, the hydrophilic-hydrophobic interface of the bilayer membrane formed of an assembly of cationic amino acid type lipids in an aqueous solution is stable and thus a vesicle structure is easily formed. Therefore, the compound represented by formula (I), when used as a lipid component of the molecular assembly, is expected to have an effect of stabilizing the vesicle structure and also the dispersed state. It is more preferable that n is 2 because this allows glutamic acid or a derivative thereof to be usable as a material of the compound represented by formula (I), which realizes low cost and low toxicity, in addition to providing the above-described effects.

Specifically, the cationic amino acid type lipid of the present invention is preferably a compound represented by the following formula (I)-1:

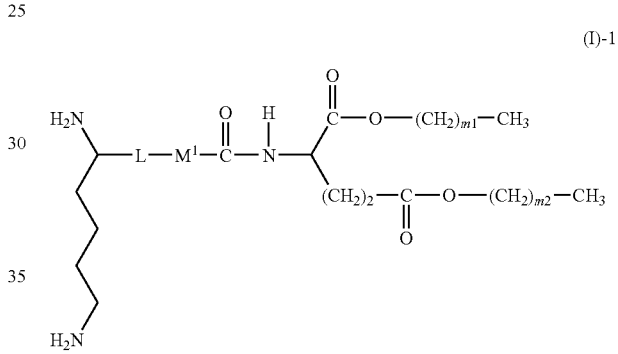

(I)-1

(wherein in formula (I)-1: L is a single bond, —CONH—, or —S—S—; $M^1$ is —$(CH_2)_k$— or —$(CH_2CH_2O)_k$— (wherein k is an integer between 0 and 14 (preferably between 0 and 11, more preferably between 1 and 11, and even more preferably between 3 and 5)); and m1 and m2 are each independently an integer between 11 and 21 (in this regard, when providing a reagent for introducing a gene into a cell and a kit for introducing a gene into a cell comprising the reagent (described below), the case where both m1 and m2 are 15 is excluded)).

Specific examples of the cationic amino acid type lipid represented by formula (I)-1 include a cationic amino acid type lipid represented by formula (I)-2:

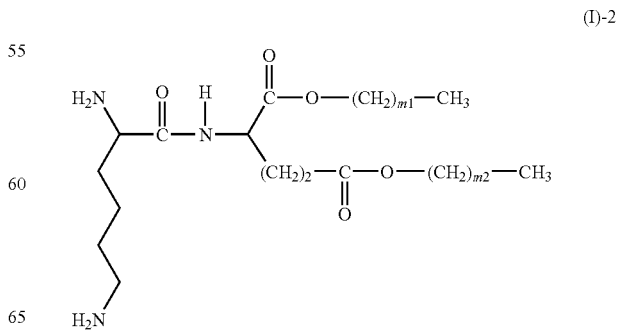

(I)-2

(wherein in formula (I)-2, m1 and m2 are the same as the case of formula (I)-1).

In the present invention, a spacer ($M^1$ and L) can be linked to an amino acid-derived cationic functional group portion in the compound represented by formula (I). When using the compound represented by formula (I) as a reagent for introducing a protein or gene, a spacer $M^1$ is represented by —$(CH_2)_k$— or —$(CH_2CH_2O)_k$—, and k is an integer between 0 and 14. Further, L is a single bond, —CONH—, or —S—S—. By introducing the spacer, the ζ potential (zeta potential) can be adjusted.

The present invention also provides a compound represented by the following formula (I') (cationic amino acid type lipid) into which a spacer $M^2$ and/or L is introduced:

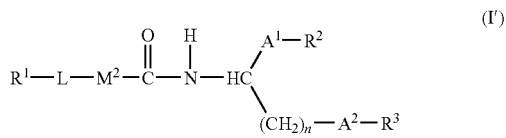

(I')

(wherein in formula (I'): $R^1$, $R^2$, $R^3$, A', $A^2$, L and n are the same as described above; and $M^2$ is —$(CH_2)_{k'}$— or —$(CH_2CH_2O)_{k'}$— (k' is an integer between 1 and 14)).

The lipid into which a spacer is introduced is preferably a compound represented by the following formula (I)-3:

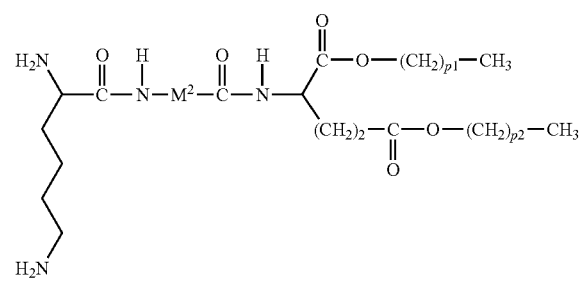

(I)-3

(wherein in formula (I)-3: $M^2$ is —$(CH_2)_{k'}$— or —$(CH_2CH_2O)_{k'}$— (wherein k' is an integer between 1 and 14 (preferably between 1 and 11, and more preferably between 3 and 5)); and p1 and p2 are each independently an integer between 11 and 21).

Specific examples of the cationic amino acid type lipid represented by formula (I)-3 include a cationic amino acid type lipid represented by formula (I)-4:

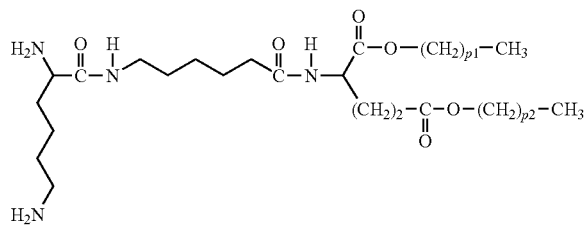

(I)-4

(wherein in formula (I)-4, p1 and p2 are the same as the case of formula (I)-3).

In the present invention, preferred examples of the lipid into which a spacer is introduced also include a cationic amino acid type lipid represented by the following formula (I)-5:

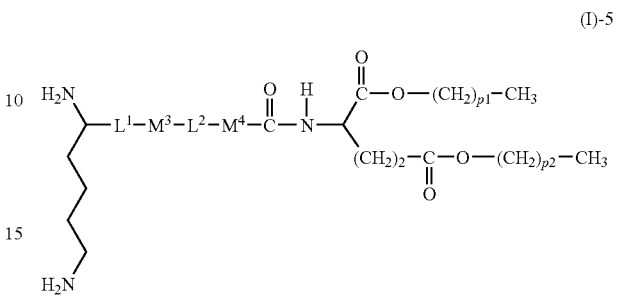

(I)-5

(wherein in formula (I)-5: $L^1$ is a single bond, —CONH—, —NICO— or —S—S—; $M^3$ is —$(CH_2)_i$—, —$(CH_2CH_2O)_i$— or —$CH^1_{i'}$—$(CH_2CH_2O)_i$—$(CH_2)_{i''}$— (wherein i is an integer between 0 and 14 (preferably between 0 and 11, more preferably between 1 and 11, and even more preferably between 3 and 5); i' is an integer between 1 and 10 (preferably between 1 and 5, and more preferably between 1 and 3); and i" is an integer between 1 and 10 (preferably between 1 and 5, and more preferably between 1 and 3)); $L^2$ is a single bond, —CONH—, —NHCO— or —S—S—; $M^4$ is —$(CH_2)_j$—, —$(CH_2CH_2O)_j$— or —$CH_{j'}$—$(CH_2CH_2O)_j$—$(CH_2)j''$— (wherein j is an integer between 0 and 14 (preferably between 0 and 11, more preferably between 1 and 11, and even more preferably between 3 and 5); j' is an integer between 1 and 10 (preferably between 1 and 5, and more preferably between 1 and 3); and j" is an integer between 1 and 10 (preferably between 1 and 5, and more preferably between 1 and 3)); and p1 and p2 are the same as the case of formula (I)-3).

As the cationic amino acid type lipid represented by the above-described formula (I)-5, for example, a compound represented by Compound 9 in the working example described below is preferred.

1-2) Method for Producing Cationic Amino Acid Type Lipid

The cationic amino acid type lipid of the present invention can be produced very easily by combining known reactions. For example, the cationic amino acid type lipid of the present invention can be produced by sequentially reacting a trifunctional core compound having the following formula with a source of a chain hydrocarbon group and with a source of a hydrocarbon group having a cationic functional group:

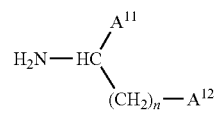

(wherein: $A^{11}$ and $A^{12}$ are each independently a carboxyl group, a hydroxyl group, or an amino group; and n is an integer of 1 to 4).

A typical synthetic route for producing the cationic amino acid lipid of the present invention is as follows.

First, the $A^{11}$ or $A^{12}$ part of the trifunctional core compound is reacted with a source of a chain hydrocarbon group. At this point, it is preferable that a functional group to be reacted with a source of a hydrocarbon group having a cationic functional group is protected with a protective group such as a tert-butoxycarbonyl group or the like according to need.

Next, an amino group of the resultant compound is reacted with the source of the hydrocarbon group having the cationic functional group. It is preferable that an amino group of the source of the hydrocarbon group having the cationic functional group is protected by a tert-butoxycarbonyl group or the like in advance and a carboxyl group to be reacted is activated by succinimide or the like in advance. The reactions are preferably performed in the presence of a catalyst such as tertiary amine or the like.

When introducing a spacer, the compound into which the chain hydrocarbon group is introduced is reacted with a source of a hydrocarbon group having a cationic functional group and a carboxyl group. As the hydrocarbon group having the cationic functional group and the carboxyl group, a compound, which has an amino group protected by a tert-butoxy group or the like at its one end and a carboxyl group at the other end, is preferably used. The portion of the hydrocarbon group may be oligooxyethylene.

The above-described reactions can be both performed at room temperature. The reactions may be performed either under elevated pressure, reduced pressure or atmospheric pressure, but is preferably performed under atmospheric pressure because the operation is simple.

After the reactions completed, the resultant product is deprotected by treatment with an acid such as trifluoroacetic acid, and is purified by a usual method. In this manner, a cationic amino acid type lipid can be obtained. The termination point of the reactions can be confirmed by gas chromatography, high performance liquid chromatography, mass spectroscopy, thin layer chromatography, nuclear magnetic resonance spectroscopy, infrared absorption spectroscopy or the like.

The method for producing the cationic amino acid type lipid of the present invention is not limited to the above-described method. For example, an amino group of a trifunctional core compound may be firstly reacted with a source of a hydrocarbon group having a cationic functional group, and then the $A^{11}$ or $A^{12}$ part of the resultant compound may be reacted with a source of a chain hydrocarbon group.

Hereinafter, examples of material compounds usable for synthesizing the cationic amino acid type lipid of the present invention will be shown.

As the source of the chain hydrocarbon group, any compound having a reactive functional group which can be covalently bonded to a trifunctional core compound, for example, an amino group, a hydroxyl group, a carboxylic group or the like is usable with no specific limitation.

Examples of the source of the chain hydrocarbon group having a carboxyl group include: a fatty acid such as acetic acid, propionic acid, butyric acid, valeric acid, isovaleric acid, capronic acid, enanthic acid, caprylic acid, undecanoic acid, lauric acid, tridecanoic acid, myristic acid, pentadecanoic acid, palmitic acid, heptadecanoic acid, stearic acid, nonadecanoic acid, arachic acid, behenic acid, palmitoleic acid, oleic acid, linoleic acid, linolenic acid, arachidonic acid and the like; branched chain forms thereof; and acid anhydrides and acid chlorides thereof.

Examples of the source of the chain hydrocarbon group having an amino group include: a straight chain primary amine such as dodecylamine, tridecylamine, tetradecylamine, pentadecylamine, hexadecylamine, heptadecylamine, octadecylamine, docosylamine, oleylamine and the like; branched chain forms thereof; and an amine such as branched isoprenoid or the like. Examples of the source of an aliphatic hydrocarbon group having an amino group include: a secondary amine such as N-methyl-dodecylamine, N-methyl-tetradecylamine, N-methyl-hexadecylamine, N-ethyl-dodecylamine, N-ethyl-tetradecylamine, N-ethyl-hexadecylamine, N-propyl-dodecylamine, N-propyl-tetradecylamine, N-propyl-hexadecylamine, dioleylamine and the like; and branched chain forms thereof.

Examples of the source of the chain hydrocarbon group having a hydroxyl group include a straight chain primary saturated alcohol such as lauryl alcohol, cetyl alcohol, stearyl alcohol, behenyl alcohol and the like. Examples of other compounds usable as the chain hydrocarbon group having a hydroxyl group include: straight chain primary saturated alcohol such as 1,1-dodecenol, 1-oley alcohol, linolenyl alcohol or the like; branched primary saturated alcohol; branched primary unsaturated alcohol; secondary saturated alcohol; and secondary unsaturated alcohol. Dialkylglycerol obtained by linking such an alcohol to the 1,3-position or 1,2-position of glycerin, and dialkylglycerol formed of a primary saturated alcohol and a primary unsaturated alcohol are also usable.

As the source of the chain hydrocarbon group, a sterol is also usable. Examples of the sterol include cholesterol, cholestanol, sitosterol, ergosterol and the like As the source of the hydrocarbon group having a cationic functional group, an amino acid or a derivative thereof is usable. In particular, lysine or a derivative thereof is preferred. The "derivative of an amino acid" encompasses compounds obtained as a result of a hydrogen atom contained in the amino acid being substituted with a substituent such as lower alkyl group (methyl, ethyl, propyl, isopropyl, n-butyl, sec-butyl, etc.), aminoalkyl group (aminomethyl, aminoethyl, aminopropyl, aminobutyl, etc.), corresponding oligoaminoalkyl group, hydroxyl group, hydroxyalkyl group (hydroxymethyl, hydroxyethyl, hydroxypropyl, etc.), oligooxyalkyl group (oligooxymethyl group, oligooxyethyl group, oligooxypropyl, etc.) or the like.

In the present invention, the above-described lipid can be used solely, or can be mixed with 1,2-dioleoyl-sn-glycero-3-phosphatidylcholine (DOPC) to form a complex. This promotes fusion between the lipid and an endosome membrane, and as a result, a protein can be introduced with high efficiency. When forming a complex of the lipid and DOPC, the mixing ratio of the lipid to DOPC is, for example, 1:1 to 10:1, and preferably 3:1 to 5:1.

2. Composition

Next, a composition to be used as the reagent of the present invention will be described. In the present invention, a composition may be in the form of a molecular assembly dispersed in an aqueous medium or in the form of a dried product produced by drying by freeze-drying, spray drying or the like.

2-1) Molecular Assembly

In the present invention, a molecular assembly may be anything which includes the cationic amino acid type lipid of the present invention described above as a constituent lipid with no specific limitation. Examples of the molecular assembly include a polymer assembly, a polymer micelle, an emulsion, a lipid microsphere, a bilayer membrane vesicle (liposome), an assembly having a hexagonal structure, and other tubular or cubic-like assemblies. In the present invention, in view of the purpose of including a protein or gene, a product having a vesicle structure such as liposome is preferred. The content of the cationic amino acid type lipid of the present invention is not limited to any specific value, but is preferably 20 to 100 mol %, and more preferably 50 to 100 mol %, based on the total molarity of the constituent lipid included in the molecular assembly.

In the present invention, the composition preferably includes an amphipathic molecule to which a polyethylene glycol chain is bound. The molecular weight of polyethylene glycol is 1,000 to 20,000, and preferably 2,000 to 6,000.

Other constituent lipids included in the molecular assembly of the present invention can form a molecular assembly with the cationic amino acid type lipid of the present invention. Such other constituent lipids are not particularly limited as long as they are generally used as constituent lipids of a molecular assembly. Examples thereof include phospholipid, fatty acid, sterols, various types of glycolipids and the like.

Examples of the phospholipid include egg yolk lecithin, soybean lecithin, hydrogenated egg yolk lecithin, hydrogenated soybean lecithin, diacylphosphatidylcholine, diacylphosphatidylethanolamine, sphingomyelin and the like. In the present invention, one or two acyl chains of diacylphosphatidylcholine or diacylphosphatidylethanolamine is preferably an oleoyl group. These phospholipids may include an unsaturated part such as ene (double bond), in (triple bond), diene, diin, triene or the like, or may include a polymerizable group such as vinyl group, for example, styryl group. The content of the phospholipid is not limited to any specific value, but is preferably 0 to 70 mol %, and more preferably 0 to 50 mol %, based on the total molarity of the constituent lipids included in the molecular assembly.

As the fatty acid contained in an acyl chain of the phospholipid, a saturated or unsaturated fatty acid having 12 to 22 carbon atoms is used. Examples thereof include myristic acid, palmitic acid, stearic acid, oleic acid, linoleic acid, linolenic acid, octadeca-2,4-dienoic acid and the like. Instead of a material having a glycerol backbone, a trifunctional amino acid such as glutamic acid or the like, a zwitterionic amino acid type lipid having a lysine backbone and the like are also usable. The content of the fatty acid is not limited to any specific value, but is preferably 1 to 70 mol %, and more preferably 5 to 30 mol %, based on the total molarity of the constituent lipids included in the molecular assembly.

To the molecular assembly, a sterol usable as a stabilizer may be added as a membrane component of the lipid vesicle. Examples of such sterols include all the steroids having a perhydrocyclopentanophenanthrene backbone such as ergosterol, cholesterol and the like. Cholesterol is preferred. There is no specific limitation on the content of the sterol. In consideration of the stability of the vesicular membrane, the content of the sterol is preferably 5 to 50 mol %, and more preferably 15 to 40 mol %, based on the total molarity of the constituent lipids included in the molecular assembly.

There is no specific limitation on the method for preparing the molecular assembly, and any generally known method is usable. For example, a liposome may be produced as follows. Powder or thin film of a single type of lipid or a mixture of lipids is hydrated and dispersed, and then subjected to a high pressure extrusion method, an ultrasonic radiation method, a stirring (vortex mixing, homogenizer) method, a freezing and thawing method, a microfluidizing method or the like. Alternatively, a single type of lipid or a mixture of lipids is dissolved in an organic solvent, the resultant solution is injected into an aqueous phase, and then the organic solvent such as ethanol, ether or the like is removed at reduced pressure or by dialysis. Still alternatively, a single type of lipid or a mixture of lipids is dispersed in an aqueous phase together with a surfactant such as sodium cholate, sodium dodecyl sulfate, Triton X-100, laurylether or the like to form an emulsion, and then the surfactant is removed by dialysis. Also, a reverse phase evaporation method, an incubation method and the like are usable.

The particle size of the molecular assembly can be freely controlled by the combination of the above-described production methods. However, the particle size of the molecular assembly is preferably 50 to 2,000 nm, and more preferably 100 to 500 nm.

2-2) Dried Product

A dried product to be used in the present invention can be obtained by drying the above-described lipid or molecular assembly. There is no specific limitation on the drying treatment, but the treatment is preferably freeze-drying or spray drying.

For example, in the freeze-drying treatment: the above-described lipid or molecular assembly is sterilized: after that, a predetermined amount thereof is put into a vial and dispersed in pure water, saline, buffer solution or the like; the lipid-dispersed solution is frozen using liquid nitrogen or the like; and after that, the frozen material is dried under reduced pressure at 15 to 30° C. As a protective agent for freeze-drying, sucrose, trehalose or the like may be dissolved in the lipid-dispersed solution in advance. Finally, the inside of the vial is subjected to substitution with nitrogen gas, thereby obtaining a freeze-dried product.

In the spray-drying treatment, for example, a solution or a fine particle-dispersed liquid may be sprayed in bursts in thermal air current. In this manner, a fine particle-type dried product can be obtained. Spray drying can be carried out using a publicly-known spray drier.

At the time of using the dried product of the present invention, any redispersion solution may de added thereto for preparation. Examples of the redispersion solution include pure water, saline, phosphate buffer solution, and phosphate buffered saline.

3. Reagent and Kit for Introducing Protein or Gene

In the present invention, the composition comprising the compound represented by formula (I) can be used as a reagent for introducing a protein.

In the present invention, the "protein" targeted for introduction of a protein into a cell refers to any peptide or polypeptide, and it is not limited by the molecular weight or the length of amino acid sequence. The above-described protein may be a monomer or multimer. Moreover, the protein may be one type of protein or a mixture of a plurality of types of proteins. The amount of protein to be encapsulated in the composition can be suitably set depending on the type and amount of a protein to be introduced into a cell, but is preferably set so as to prevent denaturation of the protein and influence on the structure of a molecular assembly in which a protein is encapsulated (in particular, the structure of a bilayer membrane vesicle), particle size, membrane stability and dispersion stability.

In the present invention, the "gene" to be targeted for gene introduction into a cell means any nucleic acid or polynucleotide regardless of the presence/absence of expression of protein, and it may be, for example, DNA or RNA. It may also be peptide nucleic acid (PNA) or a nucleic acid derivative such as LNA (Locked Nucleic Acid). Moreover, the gene also includes a recombinant vector in which a gene is incorporated into a suitable plasmid. The amount of gene to be encapsulated in the composition can be suitably set depending on the type and amount of a gene to be introduced into a cell, but is preferably set so as to provide a nucleic acid with a small number of bases (base pairs) and a high concentration.

A method for encapsulating a protein or gene into such a molecular assembly may be suitably selected depending on the type, etc. of the protein or gene.

When the water solubility of a protein to be encapsulated is high, freeze-dried mixed lipid powder is dispersed in an aqueous solution of the protein, and after it is hydrated sufficiently, the protein can be encapsulated, for example, by the extrusion method. In addition, by the combination with the freeze-drying method, the encapsulation efficiency can be increased. When the water solubility of a protein to be encapsulated is low, the protein and mixed lipid are dispersed in an aqueous solution of a surfactant such as laurylether to provide a state of mixed micelle, and by removing the surfactant by means of dialysis or ultrafiltration, the protein can be encapsulated. Non-encapsulated proteins can be separated from encapsulating vesicles by gel filtration, ultracentrifugation, ultrafiltration membrane treatment or the like.

When a gene to be encapsulated is a high-molecular-weight nucleic acid such as plasmid, for example, according to a publicly-known method, preparation can be carried out by encapsulating the gene in a giant molecular assembly having the size of several tens of μm, or by covering the gene with a cationic polymer to neutralize the charge. When a substance to be encapsulated is a low-molecular-weight nucleic acid such as decoy DNA (double-stranded DNA), siRNA and antisense DNA, in addition to the above-described method, for example, preparation can be carried out by stirring and dispersion in an aqueous solution of nucleic acid after the formation of molecular assembly. Non-encapsulated DNA or RNA can be separated from encapsulating vesicles by gel filtration, ultracentrifugation, ultrafiltration membrane treatment or the like.

The amount of the reagent for introducing a protein of the present invention is about 0.1 to 200 pmol, and preferably about 0.1 to 10 pmol per $1 \times 10^4$ cells, but can be suitably set based on a use amount of Profect 1, BioPORTER or the like, which is conventionally used as a reagent for introducing a protein. By employing the above-described use amount, a protein can be efficiently introduced.

The amount of the reagent for introducing a gene of the present invention is about 0.001 to 200 pmol, preferably about 0.001 to 100 pmol, and more preferably about 0.1 to 10 pmol per $1 \times 10^4$ cells, but can be suitably set based on an amount of a liposome reagent having a cationic lipid as a constituent lipid such as Lipofectamine, Transome, DOTAP and DMRIE, which is conventionally used as a reagent for gene introduction. The above-described use amount realizes the introduction efficiency equal to that of the conventional reagent for gene introduction (Lipofectamine) without cytotoxicity.

In general, as the particle size of a molecular assembly to be used for introduction of a protein or gene, various sizes may be used, and there is no particular limitation on this. However, in view of the effect of introduction of a protein or gene and cytotoxicity, the particle size of the molecular assembly reagent is preferably 50 to 2,000 nm, and more preferably 100 to 500 nm.

The present invention further provides a kit for introducing a protein or gene comprising the above-described reagent. A buffer solution, a pH adjuster, a cell protection solution, etc. can be used solely or in combination to be included in the kit. According to need, a standard protein, which is used as a control, or a standard nucleic acid, which is used as a control for transfection, may be included in the kit. Examples of such standard proteins include a reporter and a marker protein (e.g., luciferase, β-galactosidase and GFP). Examples of standard nucleic acids include a nucleic acid encoding a reporter or a marker protein (e.g., luciferase, β-galactosidase and GFP), and the nucleic acid may be in the form of plasmid vector. Moreover, according to need, the kit of the present invention may include, for example, a reagent for transfection enhancement such as DEAE dextran and other additives. The kit of the present invention may further include an instruction for introducing a protein or gene into a cell. Each component included in the kit may be, for example, in the state of being packaged, wherein each component is encapsulated in a container.

EXAMPLES

Hereinafter, the present invention will be described in more detail based on working examples, but the present invention is not limited thereto.

Example 1

Synthesis of the Cationic Amino Acid Type Lipid (A) A benzene solution (100 mL) of p-toluenesulfonic acid hydrate (4.56 g, 24 mmol) was subjected to boiling point reflux at 85° C., and water was removed before the reaction using Dean-Stark apparatus. Glutamic acid (2.96 g, 20 mmol) and hexadecylalcohol (10.7 g, 44 mmol) were added to the reaction solution, and subjected to boiling point reflux for 10 hours while the generated water was removed. As the reaction proceeded, the suspension was gradually dissolved to become transparent.

After the reaction completed, the solvent was removed under reduced pressure. The resultant solution was dissolved in chloroform, and washed with a saturated aqueous solution of sodium carbonate 3 times. The chloroform layer was dehydrated with magnesium sulfate. The resultant substance was filtered, and then the solvent was removed under reduced pressure. The residue was recrystallized with methanol at 4° C. to obtain a diacylglutamic acid derivative (1) (yield: 83%) as white powder.

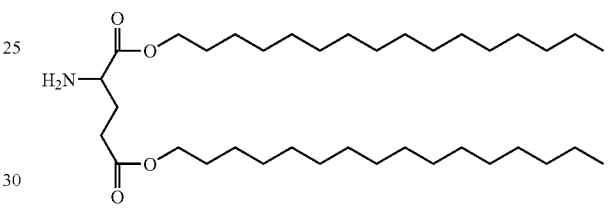

(1)

The analytical results of the diacylglutamic acid derivative (1) were as follows: Thin layer chromatography (silica gel plate, chloroform/methanol (4/1) (volume/volume): $R_f$: 0.83 (monospot))

Infrared absorption spectrum (cm$^{-1}$): 1737 ($v_{C=O}$, ester)

$^1$H-NMR (CDCl$_3$, 500 MHz, δppm): 0.89 (t, 6H, —CH$_3$); 1.25 (s, 52H, —CH$_2$—CH$_2$—); 1.62 (m, 4H, —CO—O—C—CH$_2$); 1.84 (m, 1H, glu β-CH$_2$); 2.08 (m, 1H, glu (3-CH$_2$); 2.45 (t, 2H, glu γ-CH$_2$); 3.45 (t, 1H, glu α-CH); 4.06, 4.10 (t, 4H, —CO—O—CH$_2$). MS (ESI) Calcd: 595.9. Found: 597.3 (MH)$^+$.

(B) The diacylglutamic acid derivative 1 obtained in step (A) (1.0 g, 1.67 mmol) and triethylamine (202 mg, 2.0 mmol) were dissolved in dichloromethane (30 mL) and stirred at room temperature for 1 hour. Then, lysine (617 mg, 1.4 mmol) having an amino acid protected with a t-butoxycarbonyl group, which was activated by succinimide, was added thereto and stirred at room temperature for another 6 hours.

After the reaction completed, the solvent was removed under reduced pressure. The resultant solution was dissolved in chloroform, and washed with a saturated aqueous solution of sodium carbonate 3 times. The chloroform layer was dehydrated with magnesium sulfate. The resultant substance was filtered, and the solvent was removed under reduced pressure. The residue was recrystallized with methanol at 4° C. and filtered with a glass filter (G6) to obtain a lysine derivative having a protected amino group.

Fluoroacetic acid (20 mL) was added to the resultant derivative and stirred at 4° C. for 2 hours. After the reaction completed, the solvent was removed under reduced pressure. The resultant solution was dissolved in chloroform, and washed with a saturated aqueous solution of sodium carbonate 4 times. The chloroform layer was dewatered with magnesium sulfate. The resultant substance was filtered, and the solvent was removed under reduced pressure. The residue was recrystallized with methanol at 4° C., filtered and dried to obtain a cationic amino acid type lipid 2 (yield: 80%) as white powder.

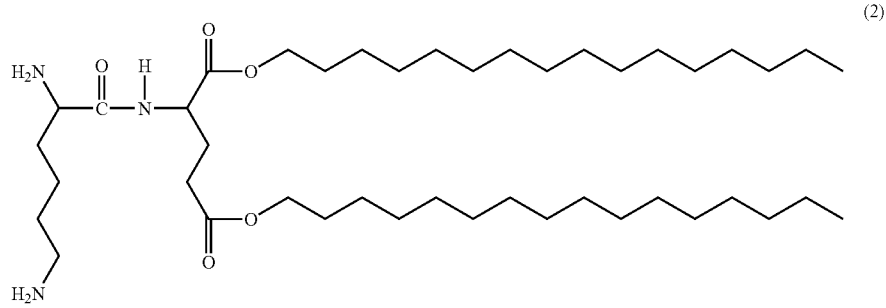

(2)

The analytical results of the cationic amino acid type lipid 2 were as follows: Thin layer chromatography (silica gel plate, chloroform/methanol (4/1) (volume/volume): $R_f$: 0.63 (monospot))
Infrared absorption spectrum (cm$^{-1}$): 1737 ($v_{C=O}$, ester); 1673 ($v_{C=O}$, amide).
$^1$H-NMR (CDCl$_3$, 500 MHz, δ(ppm)): 0.88 (t, 6H, —CH$_3$); 1.25-1.29 (br, 44H, —CH$_2$—); 4.51 (d, 1H, —CO—N—CH—); 7.8, 8.2 (br, 2H, —C—NH$_2$).

Example 2

Confirmation of Introduction of Dmc1 into Cell Nucleus Using Dmc1-Encapsulated Cationic Liposomes The present inventors focused their attention on Dmc1 protein, which plays an important role in the mechanism of homologous recombination of DNA during meiotic cell division. Dmc1 derived from human is a kind of protein (pI=5.6, 37 kDa), and it has been clear that it has a ring structure consisting of an octamer (T. Kinebuchi, et al., Molecular Cell, 2004, 14, 363-374). Also during periods other than that of meiotic cell division, the mechanism of homologous recombination is used in repair of DNA which has a serious damage such as double strand break. An error or the like at the time of repair of such DNA damage may cause mutation of DNA, and it is known that this causes cancer or genetic diseases. The present inventors thought that, when Dmc1, which is expressed only in a cell during meiotic cell division, is introduced into a somatic cell from outside, a DNA having damage or mutation would be correctly repaired by Dmc1-dependent homologous recombination, and that therefore it would be possible to apply this mechanism to cellular therapy for cancer or the like. In the below-described working example, a test for confirming whether or not Dmc1 can be introduced into a cell nucleus using a Dmc1-encapsulated cationic liposomes was carried out.

2.1. Preparation of Dmc1-Encapsulated Liposomes
2.1.1. Preparation of Freeze-Dried Lipid
As a mixed lipid (liposome), DOPC/chol/cationic lipid 2/PEG-Glu2C$_{18}$ (molar ratio: 2.5/2.5/5/0.03) was used.
Firstly, to all the components of the mixed lipid having the predetermined mixing ratio, tert-butyl alcohol was added in an amount to allow complete dissolution thereof, and the mixture was heated and melted at 60° C. The resultant mixture was freeze-dried, and powder obtained was used as the mixed lipid.
Lipid molecules constituting the liposome are shown below:

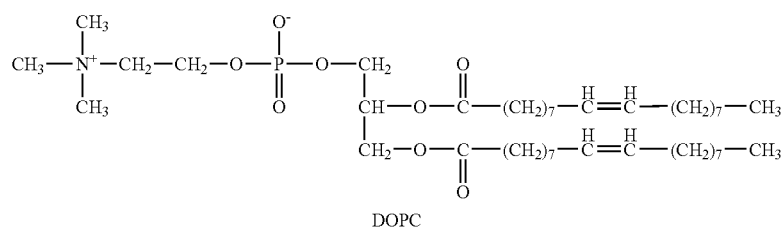

DOPC

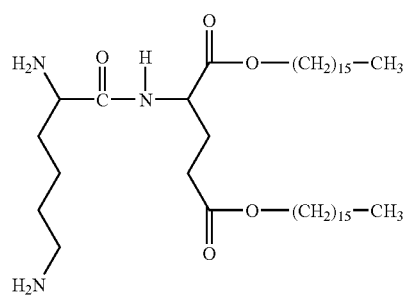

Lys-Glu2C16

-continued

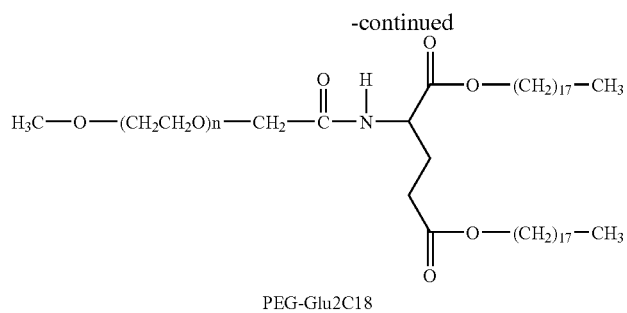

PEG-Glu2C18

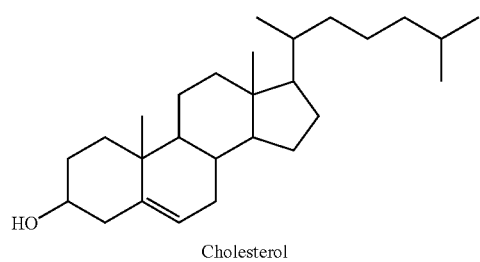

Cholesterol 2.1.2. Preparation of Liposomes

Firstly, Dmc1 was diluted to 18 μM using 20 mM HEPES buffer (pH 7.4). In this Dmc1 solution (18 μM), the mixed lipid prepared in item 2.1.1. above was stirred at room temperature for 3 hours using the hydration process, which is the ordinary method. The ratio of the lipid to Dmc1 was 75:1. After stirring, the particle size of the liposomes was controlled to some extent by means of extrusion (PVDF filter: pore size: 5, 0.65, 0.45×2, 0.22×2 μm). Finally, ultracentrifugation (100,000×g, 30 minutes=2) was performed to remove non-encapsulated Dmc1, and then dispersion was performed with 20 mM HEPES buffer (pH 7.4) to prepare Dmc1-encapsualted liposomes.

As evaluation of physical properties, the quantification of lipid was carried out by means of quantification of choline-type phospholipid, and quantification of encapsulated protein was carried out by means of HPLC (220 nm). In addition, the particle size and ζ potential were measured by the dynamic light scattering method (BECKMAN COULTER, N4 PLUS).

2.2. Results

The prepared liposomes had the particle size of about 300 nm and the ζ potential of +29 mV. The particle size did not change so much and was stable for at least about one month (particle size<500 nm). The percentage of Dmc1 encapsulation (the amount of Dmc1 after liposome preparation/the amount of feeding Dmc1) was about 20 to 40%, and the lipid yield (the amount of lipid after liposome preparation/the amount of feeding lipid) was about 40 to 50%.

Further, as shown in Table 1, when using PBS(−) as a dispersion medium, the particle size increased with time, and it was confirmed that the particle size can be controlled to some extent by using 20 mM HEPES buffer. The particle size of the Dmc1-encapsulated liposomes prepared using 20 mM HEPES buffer shown in Table 1 was 447±200 nm after one month passed. Thus, increase of the particle size was successfully suppressed.

Example 3

Evaluation of Cellular Uptake

Cells were seeded on a culture dish on the day before the experiment, and the cell density of the experiment day was set to 80%. COS-1 cells (cell line from African green monkey kidney) were used in the experiment, and they were incubated in the presence of serum. As a cell culture solution, serum-containing one or non-serum containing one was used. After the Dmc1-encapsulated liposomes were added to the dish ([lipid]=120 μg/φ35 mm dish), the cells were cultured at 37° C. for 4 hours, and after that, the cells were washed with PBS(−) twice, and then subjected to nuclear staining with Hoechst (room temperature, 15 minutes). The cells were washed with PBS(−) again and stained with Lysotracker, which is a lysosomal staining dye, and after that, observation thereof was carried out using a confocal microscope. Further, Dmc1 was labeled with Cy3 and intracellular dynamic state thereof was observed using the confocal microscope.

TABLE 1

Table Characteristics of liposome entrapped hDmc1.

| | | Particle size [nm] | | | |
|---|---|---|---|---|---|
| Buffer | ζ potential [mV] | just after preparation | 3 days after preparation | 5 days after preparation | 8 days after preparation |
| HEPES | +29 | 244 ± 95 | 258 ± 91 | 283 ± 103 | 260 ± 85 |
| PBS | +17 | 1162 ± 535 | 1634 ± 789 | 3813 ± 1660 | 5926 ± 2676 |

The method for labeling Dmc1 with Cy3 was as follows. Two vials of Cy3-maleimide (monofunctional dye labeling kit (GE Health Care), 300 nmol/vial) was dissolved in 20 μl of DMSO, and the mixture was subjected to 1/5 dilution with buffer. To the obtained mixture, 900 mL of Dmc1 solution (20 mg/900 mL) was added, and stirred for 10 minutes. By removing unlinked Cy3 by gel filtration, Cy3-labeled Dmc1 was obtained.

<Results>

FIG. 1 shows confocal laser microscopic images of liposome/Dmc1 complexes introduced into COS-1 cells ([Dmc1]=1.3 mM). The center portions are xy planar images, and the right and bottom portions are cross-sectional images corresponding to z-axis obtained by vertically cutting along respective red lines on the xy planar images.

Cy3-Dmc1 (red luminescent spots) was observed in the cells both in the presence and absence of serum, and Cy3-Dmc1 and endosomes (green luminescent spots) were differently localized. It was indicated that Dmc1-encapsulated liposomes (Cy3-Dmc1) was efficiently taken into cells.
Red: liposome/Cy3-Dmc1 complex
Blue: cell nucleus (Hoechst 33342)
Green: endosome (FM-1 43)
Scale bar: 20 μm Cytotoxicity of the liposomes was evaluated using Alamar blue (oxidation-reduction enzyme activity of mitochondria was measured). When incubation was performed for 4 hours, almost no cytotoxicity was observed. Even when incubation time was extended to 24 hours, about 80% of the cells survived. The results strongly suggest that Dmc1-encapsulated liposomes have a property that cytotoxicity thereof is low.

Example 4

Confirmation of Migration into the Nucleus Using Western Blotting

Dmc1 is an intranuclear protein, and in order to enable application of the protein to DNA repair, Dmc1 introduced from outside must migrate into the nucleus. In the below-described working example, analysis using Western blotting was carried out in order to examine whether Dmc1 introduced exists in cytoplasm or in nucleus.

4.1. Preparation of Cells

An experiment was carried out under the same conditions as those of the experiment of cellular uptake in Example 3. By the treatment with trypsin-EDTA, cells (COS-1) in the form of pellet were collected. The collected cells were immediately frozen for preservation at −80° C.

4.2. Separation Between Cytoplasm and Nucleus

The cytoplasm component and the cell nucleus component were separated from each other using two types of surfactants (NP-40 and SDS). After that, the total protein in each of the samples was quantified using RC-DC protein assay kit.

The pellet of cells was washed with PBS, and the cells were suspended in Buffer N containing 0.6% NP-40. This cell suspension was centrifuged (4,700 rpm, 5 minutes), and supernatant obtained was used as a cytoplasmic fraction. Meanwhile, the pellet after centrifugation was washed with Buffer N and suspended in 2×SDS sample buffer. The suspension was heated at 100° C. for 10 minutes and then centrifuged (1,500 rpm, 5 minutes), and supernatant obtained was used as a nuclear fraction.

4.3. Western Blotting

The total amount of protein in each of the cytoplasmic fraction sample, the nuclear fraction sample and Dmc1 sample (control) were set to be constant, and the samples were subjected to SDS-PAGE electrophoresis (200 v, 1 hour) and transfer to PVDF membrane (150 mA, 1 hr). After that, together with a Dmc1 antibody, a histone antibody and a tubulin antibody were also used in order to confirm separation of nucleus and cytoplasm, respectively. Finally, bands of Dmc1, tubulin and histone were detected according to the chemiluminescence method utilizing a HRP group of a secondary antibody (anti-rabbit HRP antibody).

4.4. Results

Figure 2:
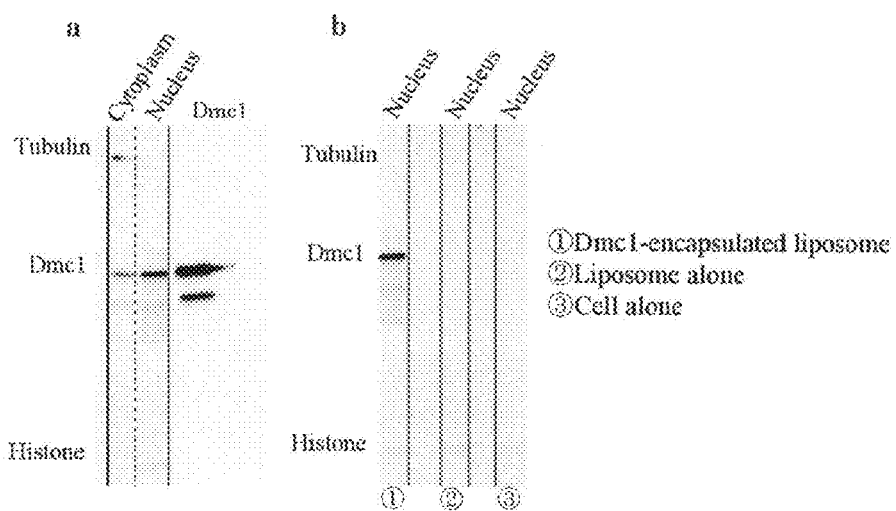
FIG. 2 shows analytical results regarding localized site of Dmc1 introduced into cells obtained by means of Western blotting.

As shown in FIG. 2a, in both the cytoplasm component and the cell nucleus component, bands were observed at the position of Dmc1. Thus, it was confirmed that Dmc1 was introduced into the nucleus when using the Dmc1-encapsulated liposome. The band of tubulin was observed only in the cytoplasm component, and the band of histone was observed only in the nucleus component. Thus, it was confirmed that the cytoplasm component and the nucleus component were correctly separated from each other.

Further, as shown in FIG. 2b, no band was observed at the position of Dmc1 of the nucleus component when using only a liposome body (non-encapsulated liposomes) or only an intact cell which is not encapsulated in a liposome. Thus, it was confirmed that the band regarding the Dmc1-encapsulated liposomes was derived from Dmc1. The results showed that the Dmc1 introduced by the liposome migrated into the nucleus. Thus, it is indicated that the Dmc1-encapsulated liposomes have a function to transfer Dmc1 to an appropriate site in a cell (the nucleus in this case).

Example 5

Confirmation of Introduction of Dmc1-Encapsulated Liposomes into a Cell Other than COS-1

In order to confirm whether or not the Dmc1-encapsulated liposomes are taken into a cell other than COS-1 cell (cell line from African green monkey kidney), an experiment of cellular uptake was carried out using NIH-3T3 cells (fibroblast cells derived from mouse embryo).

As the Dmc1-encapsulated liposomes, the same product as that prepared in Example 2 was used. Evaluation of cellular uptake was carried out in a manner similar to that in Example 3, except that NIH-3T3 cells were used instead.

<Results>

Figure 3:
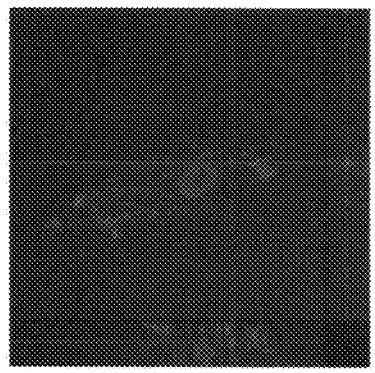
FIG. 3 shows confocal laser microscopic images of liposome/Dmc1 complexes introduced into NIH-3T3 cells.

As shown in FIG. 3, Cy3-Dmc1 (red luminescent spots) was observed in the NIH-3T3 cells, and Cy3-Dmc1 and endosomes (green luminescent spots) were differently localized. Thus, it was confirmed that Cy3-Dmc1 was taken into the NIH-3T3 cells. Therefore, it was confirmed that Dmc1 was taken into cytoplasm in a cell other than COS-1 cell when using Cy3-Dmc1-encapsulated liposomes.
Introduction: Cy3-Dmc1-encapsulated liposomes
Cell: NIH-3T3
Red: Cy3-Dmc1
Blue: cell nucleus
Green: endosome Example 6

Confirmation of Introduction of Protein Other than Dmc1 into a Cell Using Liposomes In order to confirm whether or not the liposome used (DOPC/choUcationic lipid 2/PEG-Glu2C$_{18}$ (molar ratio: 2.5/2.5/5/0.03)) also has the ability to introduce other proteins into a cell, evaluation of cellular uptake of albumin was carried out using a TRITC (rhodamine)-labeled albumin (rHSA)-encapsulated liposomes.

6.1. Preparation of TRITC-rHSA-Encapsulated Liposomes 6.1.1. TRITC Labeling to rHSA Firstly, TRITC (2 mg) was vortexed in 0.1N NaOH (200 μl). PBS (−, 600 μl) was further added thereto, and the mixture was vortexed to prepare TRITC solution (5.64 mM). The TRITC solution was added to rHSA, and the mixture was stirred. After that, free TRITC was removed with a column (Sephadex G25) to provide a TRITC-labeled rHSA (TRITC-rHSA). When passing through a column, 20 mM HEPES buffer was used. The prepared TRITC-rHSA was subjected to quantification of rHSA according to the biuret method.

6.1.2. Preparation of TRITC-rHSA-Encapsulated Liposomes

Preparation was carried out in a manner similar to that in Example 2, except that Dmc1 in the preparation of the Dmc1-encapsulated liposome was replaced by TRITC-rHSA. Firstly, the prepared TRITC-rHSA was diluted to 18 μM using 20 mM HEPES buffer (pH 7.4). In this TRITC-rHSA solution (18 μM), the mixed lipid prepared in item 2.1.1. in Example 2 was stirred at room temperature for 3 hours, and the particle size was equalized by means of extrusion (PVDF filter: pore size: 5, 0.65, 0.45×2, 0.22×2 μm). Finally, ultracentrifugation (100,000×g, 30 minutes×2) was performed to remove non-encapsulated TRITC-rHSA, and then dispersion was performed with 20 mM HEPES buffer (pH 7.4) to prepare TRITC-rHSA-encapsulated liposomes.

As evaluation of physical properties, the quantification of lipid was carried out by means of quantification of choline-type phospholipid, and quantification of encapsulated protein was carried out by means of HPLC (220 nm). In addition, the particle size was measured by the dynamic light scattering method.

<Results>

The prepared TRITC-rHSA liposomes had the particle size of about 300 nm. It was confirmed that the particle size did not change so much (<500 nm) and was stable for at least about one week.

6.2. Evaluation of Cellular Uptake of TRITC-rHSA-Encapsulated Liposomes

The liposome composition was DOPC/chol/cationic lipid 2/PEG-Glu2C$_{18}$ (molar ratio: 2.5/2.5/5/0.03), which is the same as that in Example 2. Evaluation of cellular uptake was carried out in a manner similar to that in Example 3.

Cells were seeded on a culture dish on the day before the experiment, and the cell density of the experiment day was set to 80%. COS-1 cells (cell line from African green monkey kidney) were used in the experiment, and they were incubated in the presence of serum.

Firstly, the culture solution for cells was replaced by serum-containing one or non-serum containing one, and after the addition of TRITC-rHSA-encapsulated liposomes ([lipid]=120 mg/φ35 mm dish), incubation was carried out for 4 hours. After that, the cells were washed with PBS(−) twice, and then subjected to nuclear staining with Hoechst 33342 (room temperature, 15 minutes). The cells were washed with PBS(−) again and subjected to endosome staining using Lysotracker (37° C., 5% $CO_2$, 60 min), and then observation was carried out using a confocal microscope.

<Results>

Figure 4:
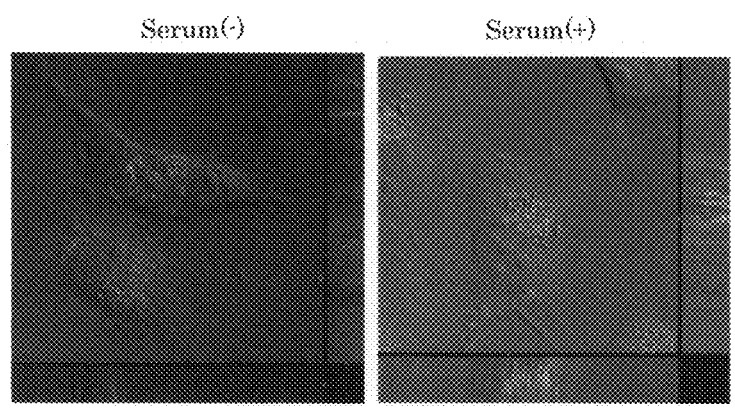
FIG. 4 shows confocal laser microscopic images of liposome/rHSA complexes introduced into COS-1 cells.

TRITC-rHSA (red luminescent spots) was observed in the cells both in the presence and absence of serum, and TRITC-rHSA and endosomes (green luminescent spots) were differently localized. Therefore, it was confirmed that TRITC-rHSA was taken in cytoplasm (FIG. 4). Thus, it was confirmed that a protein other than Dmc1 is transferred to cytoplasm in a cell when being encapsulated in liposome.

Introduction: TRITC-rHSA-encapsulated liposomes

Cell: COS-1

Comparative Example 1

In the Case without DOPC

Liposome composition: chol/cationic lipid 2/PEG-Glu2C$_{18}$ (molar ratio: 2.5/5/0.03)

Using the same procedures as those for the Dmc1-encapsulated liposome using DOPC/chol/cationic lipid 2/PEG-Glu2C$_{18}$ (molar ratio: 2.5/2.5/5/0.03) used in Example 2, a Dmc1-encapsulated liposome was prepared using chol/cationic lipid 2/PEG-Glu2C$_{18}$ (molar ratio: 2.5/5/0.03). The particle size was about 300 nm and stable for about 3 days after the preparation, but within one week, the liposome particles were completely aggregated and precipitated.

In the Case without Amphipathic Molecule to which a Polyethylene Glycol Chain is Bound Liposome composition: DOPC/chol/cationic lipid 2 (molar ratio: 2.5/2.5/5)

Influence of PEG-Glu2C$_{18}$ as an amphipathic molecule to which a polyethylene glycol chain is bound was examined using rHSA. Firstly, 25 wt % rHSA solution was diluted with PBS to prepare 0.4 wt % rHSA solution. To the obtained 0.4 wt % rHSA solution, a mixed lipid having the composition shown in Table 2 prepared in a manner similar to that in item 2.1. above was added, and the mixture was hydrated and stirred. The particle size was controlled to some extent by means of an extruder (PVDF filter: pore size: 5, 0.65, 0.45×2, 0.22×2 μm). Finally, ultracentrifugation (100,000×g, 30 minutes×2) was performed, and by performing redispersion using a dispersion medium (PBS), rHSA-encapsulated liposomes were obtained.

TABLE 2

Characteristics of liposomes

| | | Particle size [nm] | | |
| --- | --- | --- | --- | --- |
| Mixed lipids | Molar ration | just after preparation | 3 day after preparation | 7 day after preparation |
| DOPC/chol/Lys-Glu2C$_{16}$/PEG-Glu2C$_{18}$ | 2.5/2.5/5/0.03 | 331 ± 141 | 489 ± 219 | 788 ± 371 |
| DOPC/chol/Lys-Glu2C$_{16}$ | 2.5/2.5/5 | 1750 ± 841 | 30917 ± 14328 | 19663 ± 9304 |

As shown in Table 2, the particle size of the liposomes without using PEG-Glu2C$_{18}$ increased more than that of the liposomes using PEG-Glu2C$_{18}$. The cationic liposomes were easily aggregated via an anionic rHSA, and when the cationic liposomes were subjected to surface modification using a PEG chain, the dispersion stability thereof was significantly improved. Further, in the system using this rHSA, the rHSA encapsulation rate was increased by using PEG It was confirmed that PEG was useful for encapsulation of an anionic protein for the purpose of particle size control.

Example 7

Influence of the Difference of Liposome Surface Charge on Cellular Uptake

In the below-described working example, optimization of liposome membrane component at the time of uptake into a cell was carried out using rhodamine-labeled cationic, zwitterionic and anionic empty liposomes.

7.1. Preparation of Liposomes

The liposomes were prepared in a manner similar to that in item 2.1. in Example 2. To each of lipid components having the respective mixing ratio shown in Table 3, tert-butylalcohol was added in an amount sufficient for complete dissolution of each of the lipid components, and each of the obtained mixtures was heated and melted. Each of the resultant mixtures was freeze-dried to obtain powder as a mixed lipid.

TABLE 3

| | Liposome composition | |
|---|---|---|
| charge | mixed lipids | molar ratio |
| cationic | DOPC/chol/Lys-Glu2C$_{16}$/PEG-Glu2C$_{18}$ | 2.5/2.5/5/0.03 |
| zwitterionic | DOPC/chol/PEG-Glu2C$_{18}$ | 2.5/2.5/0.03 |
| anionic | DOPC/chol/DHSG/PEG-Glu2C$_{18}$ | 5/5/1/0.03 |

Next, in PBS(−), each of the prepared mixed lipids was stirred at room temperature for 3 hours, and the particle size was controlled to some extent by means of extrusion (PVDF filter: pore size: 5, 0.65, 0.45×2, 0.22×2 μm). Finally, ultracentrifugation (100,000×g, 30 minutes×2) was performed, and then dispersion was performed with PBS to prepare liposome. DHSG used in this working example is an anionic lipid.

7.2. Evaluation of Cellular Uptake

Evaluation was carried out in a manner similar to that in Example 3 except that endosome staining was not performed. Cells were seeded on the day before the experiment, and the cell density of the experiment day was set to 80%. COS-1 cells (cell line from African green monkey kidney) were used in the experiment, and they were incubated in the presence of serum. Firstly, the culture solution for cells was replaced by serum-containing one or non-serum containing one, and after the addition of Dmc1-encapsulated liposomes ([lipid]=120 mg/φ35 mm dish), incubation was carried out for 4 hours. After that, the cells were washed with PBS(−) twice, and then subjected to nuclear staining with Hoechst 33342 (room temperature, 15 minutes). The cells were washed with PBS(−) again, and then observation was carried out using a confocal microscope.

<Results>

Figure 5:
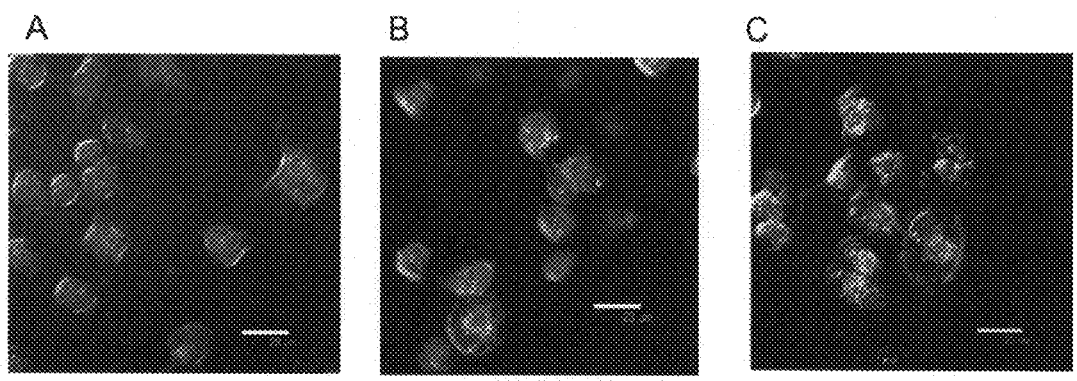
FIG. 5 shows confocal laser microscopic images of liposomes introduced into COS-1 cells.

The intracellular location of the rhodamine-labeled liposomes was examined using the nucleus stained with Hoechst 33342 as an index. As a result, the amount of cellular uptake became smaller and smaller in the cationic, anionic and zwitterionic liposomes in this order (FIG. 5). In the cases of the anionic and zwitterionic liposomes, there was only a slight amount of cellular uptake, and adsorption to cell membranes was observed. Migration of liposomes taken into cells into the nucleuses was not observed, but the liposomes and the nucleuses were present on the same surface. Thus, it was confirmed that the liposomes were taken into cells.

Comparative Example 2

Comparison with Commercially-Available Reagents for Protein Introduction

In this comparative example, comparison between the below-described 3 types of commercially-available reagents for protein introduction and the Cy3-Dmc1-encapsualted liposomes with respect to introduction of Dmc1 into cells was carried out.

Profect P-1 (lipid base) and P-2 (non-lipid base) (Targeting System): a complex was formed by being mixed with the protein solution.

BioPORTER (lipid base) (Gene Therapy Systems, Inc.): a complex was formed by forming a film and thereafter being hydrated with the protein solution.

Each introduction method was employed according to respective protocols for reagent kits. Optimization of Dmc1 introduction efficiency using the reagents for protein introduction and comparison of Dmc1 behavior in cells among the reagents utilizing observation using a confocal microscope were carried out (additive amount of Dmc1: 0.1, 1 and 5 μg/mL; and incubation time: 4 and 20 hours), and results thereof were compared to those of the cationic liposome. Note that incubation was all performed in the absence of serum. Further, cell nucleus staining and endosome staining after incubation were performed in a manner similar to that in Example 3.

In the cases of the reagents for protein introduction Profect P-1 and P-2, it seemed that Dmc1s (red luminescent spots) were adsorbed to cell surfaces, and it did not seem that Dmc1s were efficiently introduced into cells. In the case of BioPORTER, Dmc1s were observed at the position of endosomes (green luminescent spots) in cells, and behavior similar to that in the case of cationic liposomes was confirmed. When incubation time was 20 hours, in all the cases of the reagents, it seemed that many Dmc1s were adsorbed to cell surfaces.

Then, comparison between BioPORTER and the liposomes was made as follows: incubation time was 4 hours; the ratio between the amount of the reagent and the amount of Dmc1 was changed in the same way, but by controlling the amount of Dmc1 per one dish, the optimum ratio was determined; and it was compared to that in the case of the liposome. Note that the comparison was made with the amount of Dmc1 per one dish being set to 0.1 μg.

Within the cells, endosomes (green luminescent spots) and Dmc1s (red luminescent spots) were differently localized, and uptake of Dmc1 into cytoplasm was confirmed only in the case of the following ratio: 0.1 λg Dmc1+1 μl BioPORTER. This ratio was regarded as the optimum ratio of BioPORTER for Dmc1 introduction.

Further, in the previous experiment, the optimum applying amount of Dmc1 for both BioPORTER and the Dmc1-encapsulated liposomes was 1 μg per one dish. Therefore, using the optimized ratio of BioPORTER in this experiment, comparison with the case of the Dmc1-encapsulated liposomes was made again with the concentration of 1 μg/dish.

In both the cases, Dmc1 s (red luminescent spots) and endosomes (green luminescent spots) were differently localized within cells, and it was confirmed that Dmc1 was taken into cytoplasm.

Next, these two materials were compared to each other in the presence of serum.

In both the cases, it was confirmed that Dmc1 was taken into cytoplasm. The number of cells in which Dmc1 was taken into cytoplasm was a little bit larger in the case of Cy3-Dmc1-encapsulated liposomes.

Example 8

Synthesis of Spacer-Introduced Cationic Amino Acid-Type Lipid

In the mixing system with phospholipid or the like, since the hydrophilic portion of the conventional cationic lipid 2 is small, it is buried in the hydrophilic portion of DOPC. Therefore, a cationic lipid 5 in which a spacer is introduced into the position between the hydrophilic portion and the hydrophobic portion of a cationic lipid (Lys-C5-Glu2C$_{16}$) was examined.

(A) Diacylglutamic acid derivative 1 prepared in Example 1 was used.
(B) Diacylglutamic acid derivative 1 (1.0 g, 1.67 mmol) and triethylamine (202 mg, 2.0 mmol) were dissolved in 30 mL of dichloromethane, and the mixture was stirred at room temperature for 1 hour. Then, 6-aminohexanoic acid (323 mg, 1.4 mmol) having an amino group protected with a t-butoxycarbonyl group, which was activated by succinimide, was added thereto and stirred at room temperature for another 6 hours. After the reaction completed, solvent elimination and separation using a saturated aqueous solution of sodium carbonate/chloroform were performed (3 times for each). After that, dewatering with magnesium sulfate, recrystallization with methanol at 4° C. and filtration with a glass filter (G6) were performed, thereby obtaining a spacer-introduced diacylglutamic acid derivative. To the obtained derivative, fluoroacetic acid (20 mL) was added and stirred at 4° C. for 2 hours. After the reaction completed, separation using a saturated aqueous solution of sodium carbonate/chloroform were performed (×4). After that, dewatering with magnesium sulfate, recrystallization with methanol at 4° C., filtration and drying were performed, thereby obtaining a spacer-introduced amino acid type lipid 4 (Compound 4) (yield: 63%) as white powder.

compound 4

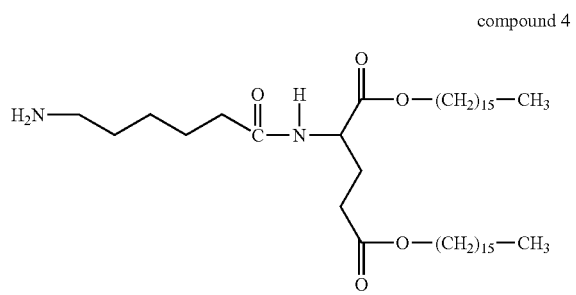

The analytical results of the spacer-introduced diacylglutamic acid derivative 4 were as follows:
Thin layer chromatography (silica gel plate, chloroform/methanol (8/1) (volume/volume): R$_f$: 0.12 (monospot)).
Infrared absorption spectrum (cm$^{-1}$): 1737 ($v_{C=O}$, ester).

$^1$H-NMR (CDCl$_3$, 500 MHz, δppm): 0.87 (t, 6H, —CH$_3$); 1.25 (s, 52H, —CH$_2$—CH$_2$—); 1.60 (m, 4H, —CO—O—C—CH$_2$); 1.73 (m, 2H, —CH$_2$—CH$_2$—CO—NH—); 1.94 (m, 1H, glu β-CH$_2$); 2.14 (m, 1H, glu β-CH$_2$); 2.25 (m, 2H, NH$_2$—CH$_2$—CH$_2$—); 2.41 (t, 2H, glu γ-CH$_2$); 2.98 (m, 2H, —CH$_2$—CH$_2$—CO—NH—); 4.04, 4.11 (t, 4H, —CO—O—CH$_2$); 4.50 (t, 1H, glu α-CH); 7.02 (d, 1H, —CO—NH—); 8.07 (br, 2H, —NH$_2$)
MS (ESI) Calcd: 709.1. Found: 709.8 (MH)$^+$.

(C) Diacylglutamic acid derivative 4 (1.0 g, 1.41 mmol) and triethylamine (171 mg, 1.69 mmol) were dissolved in 30 mL of dichloromethane, and the mixture was stirred at room temperature for 1 hour. Then, lysine (743 mg, 1.69 mmol) having an amino group protected with a t-butoxycarbonyl group, which was activated by succinimide, was added thereto and stirred at room temperature for another 6 hours. After the reaction completed, solvent elimination and separation using a saturated aqueous solution of sodium carbonate/chloroform were performed (2 times for each). After that, dehydrating with magnesium sulfate, recrystallization with methanol at 4° C. and filtration with a glass filter (G6) were performed, thereby obtaining a lysine derivative having a protected amino group. To the obtained derivative, fluoroacetic acid (20 mL) was added and stirred at 4° C. for 2 hours. After the reaction completed, separation using a saturated aqueous solution of sodium carbonate/chloroform (×4). After that, dehydrating with magnesium sulfate, recrystallization with methanol at 4° C., filtration and drying were performed, thereby obtaining a spacer-introduced cationic amino acid type lipid 5 (Compound 5) (yield: 38%) as white powder.

compound 5

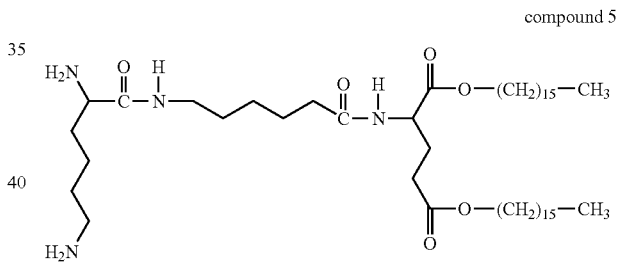

The analytical results of the spacer-introduced cationic amino acid type lipid 5 were as follows:
Thin layer chromatography (silica gel plate, chloroform/methanol (8/1) (volume/volume): R$_f$: 0.05 (monospot)).
$^1$H-NMR (CDCl$_3$, 500 MHz, δppm): 0.87 (t, 6H, —CH$_3$); 1.25 (s, 52H, —CH$_2$—CH$_2$—); 1.60 (m, 4H, —CO—O—C—CH$_2$); 1.80 (m, 1H, glu β-CH$_2$); 1.98 (m, 1H, glu β-CH$_2$); 2.38 (t, 2H, glu γ-CH$_2$); 2.93 (m, 2H, Lys . . . —CH$_2$—NH$_2$); 3.18 (m, 2H, —CO—NH—CH$_2$—CH$_2$—); 3.83 (t, 1H, Glu α-CH); 4.06, 4.11 (t, 4H, —CO—O—CH$_2$); 4.55 (m, 1H, Lys . . . —CH); 7.08 (d, 1H, —CO—NH—)
MS (ESI) Calcd: 836. Found: 837.8 (MH)$^+$.

Example 9

Preparation of Cationic Liposome

To a mixed lipid of DOPC, cholesterol and PEG-Glu2C$_{18}$, the cationic lysine-type lipid 2 or the spacer-introduced cationic amino acid type lipid (5) was added, and after the mixture was dissolved in 5 mL of t-butylalcohol, it was freeze-dried. Then, the obtained material was hydrated with 20 mM HEPES buffer so that the lipid concentration became 2 wt % (room temperature, 12 hours), and after that, the extrusion method was applied thereto to provide the final pore size of 0.22 μm. The external aqueous phase was washed by mean of ultracentrifugation, and then the concentration was adjusted by means of quantification of phospholipid, thereby preparing liposomes having the particle size of about 250 nm (Table 4).

TABLE 4

Liposome components.

| | Mixed lipid | Molar ratio |
|---|---|---|
| (a) | DOPC/chol/PEG-Glu2C$_{18}$ | 5/5/0.03 |
| (b) | DOPC/chol/Lys-Glu2C$_{16}$/PEG-Glu2C$_{18}$ | 2.5/2.5/5/0.03 |
| (c) | DOPC/chol/Lys-C$_5$-Glu2C$_{16}$/PEG-Glu2C$_{18}$ | 2.5/2.5/5/0.03 |

Example 10

Preparation of Albumin-Encapsulated Liposome 2 mg of tetramethylrhodamineisothiocyanate (TRITC) was dissolved in 0.1 N—NaOH aq, and pH thereof was adjusted to 7.4. The obtained aqueous solution was mixed with 1 mL of 25 g/dL rHSA and stirred for 6 hours. After that, unlinked rhodamine was removed using a gel column (Sephadex G-25), thereby preparing a rhodamine-labeled albumin. 30 mg of each of 3 types of mixed lipids (Table 5) was mixed with 1 mL of 3 g/dL rhodamine-labeled albumin, and after hydration for 6 hours, the resultant mixture was subjected to a high-pressure extrusion method (final pore size: 0.22 μm) to control the particle size. After that, non-encapsulated TRITC-labeled albumin was removed by ultracentrifugation (100,000×g, 30 minutes), and redispersion was performed using HEPES buffer, thereby preparing TRITC-labeled albumin-encapsulated liposomes.

Physical properties of the prepared TRITC-labeled albumin-encapsulated liposomes were measured. The ζ potential of the prepared liposomes (lipid concentration: 1 mg/mL) at pH 7.4 was measured (Table 5). Liposomes (c) in which the spacer-introduced cationic lipid 5 was introduced had the highest ζ potential, and it was indicated that the cationic portion was located at a more outer position due to the spacer. Further, using HPLC (column: Shodex protein KW-803, eluent: PB (pH 7.0)/methanol 10/1 (V/V), detection: UV 280 nm), the concentration of encapsulated rHSA was measured, and the efficiency of rHSA encapsulation in liposome and the rate of encapsulation were calculated.

TABLE 5

Characteristics of liposomes.

| | ζ potential [mV] | Efficiency of encapsulation [×10$^{-2}$] | Rate of encapsulation [%] |
|---|---|---|---|
| Liposome (a) | −6.8 | 0.280 | 1.45 |
| Liposome (b) | 25.2 | 1.62 | 16.3 |
| Liposome (c) | 29.0 | 2.12 | 16.2 |

The efficiency of rHSA encapsulation and the rate of encapsulation of the prepared liposomes are shown in Table 5. rHSA is a protein whose surface is anionic. Therefore, it is considered that the higher the ζ potential of liposome is, the larger the number of rHSAs encapsulated is.

Example 11

Introduction of Albumin-Encapsulated Liposomes into Cells

2×10$^4$ COS-1 cells (cell line from monkey kidney) were seeded on a glass bottom dish, and 24 hours later, 1 mL of liposome (lipid concentration: 2 μg/mL) was added thereto. After cultured for 4 hours, the cells were washed with PBS twice, and the nucleuses and endosomes were stained with Hoechst 33342 and LysoTracker (150 nM), respectively. Then, the dynamic state of introduction into the cells was observed using a confocal microscope.

Figure 6:
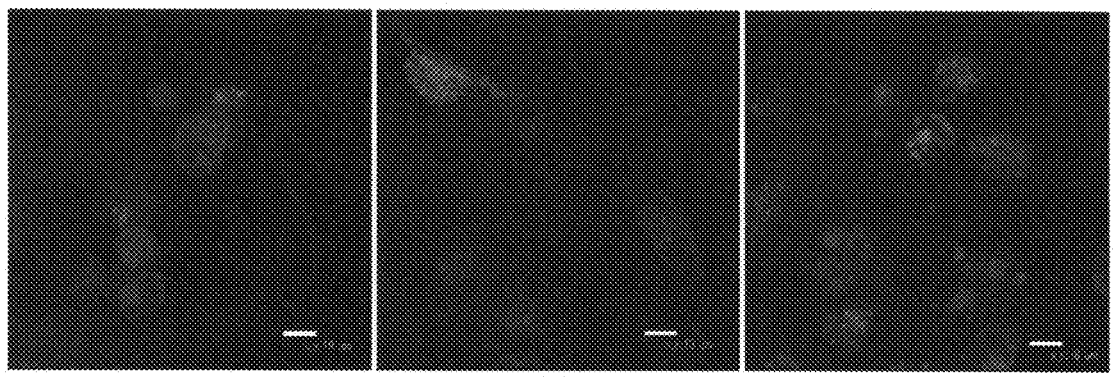
FIG. 6 shows confocal laser microscopic images of liposome/rHSA complexes introduced into COS-1 cells.

With respect to control liposomes (a) (DOPC/chol/PEG-Glu2C$_{18}$), almost no TRITC-rHSA was observed in the cells (FIG. 6, left panel). It is considered that it is because the amount of liposomes taken into the cells was small.

Next, with respect to liposomes (b) having the cationic lipid 2 as a membrane component (DOPC/chol/cationic lipid 2/PEG-Glu2C$_{18}$), many TRITC-rHSAs were observed in the cells (FIG. 6, center panel). However, many TRITC-rHSAs whose location was identical to that of endosomes were also observed.

With respect to liposomes (c) (DOPC/chol/cationic lipid 5/PEG-Glu2C$_{18}$), it seemed that the number of TRITC-rHSAs introduced was more than that in the case of liposomes (b) (FIG. 6, right panel). The ζ potential of the liposomes (b) is not much different from that of the liposomes (c) in HEPES dispersion medium. However, when added to cells, the hydrophilic portion of the cationic lipid 5 tends to easily adsorb to the cell surface, and it is thought that the above-described result indicates that the amount of introduction into cells increased.

Example 12

Synthesis of Spacer-Introduced Cationic Lipids

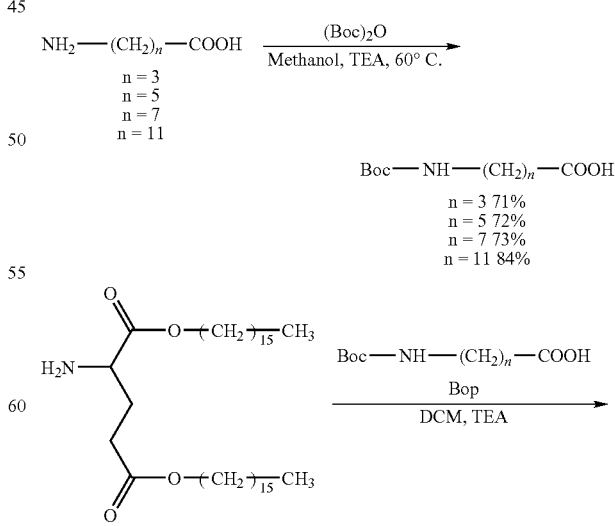

-continued

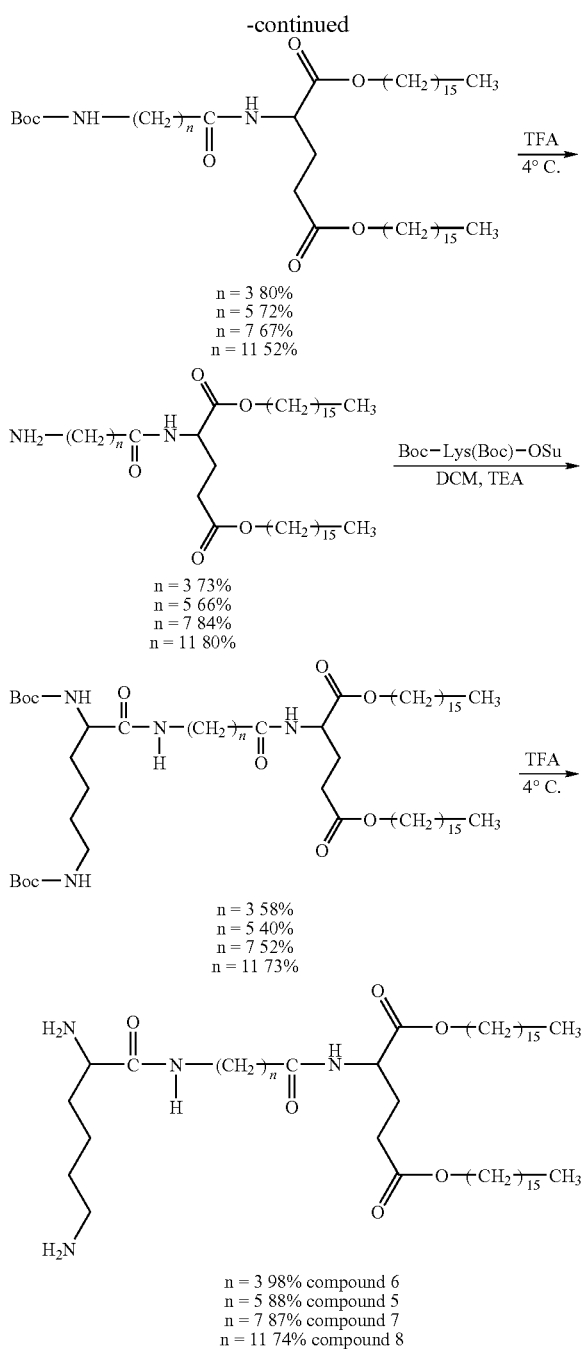

n = 3 80%
n = 5 72%
n = 7 67%
n = 11 52% n = 3 73%
n = 5 66%
n = 7 84%
n = 11 80% n = 3 58%
n = 5 40%
n = 7 52%
n = 11 73% n = 3 98% compound 6
n = 5 88% compound 5
n = 7 87% compound 7
n = 11 74% compound 8

As shown in the above-described scheme, syntheses of Lys-$(CH_2)_3$-Glu2C$_{16}$ (6), Lys-$(CH_2)_5$-Glu2C$_{16}$ (5), Lys-$(CH_2)_7$-Glu2C$_{16}$ (7) and Lys-$(CH_2)_{11}$-Glu2C$_{16}$ (8) were carried out. Hereinafter, methods for synthesizing these respective lipids will be specifically described.

(A) Method for synthesizing Lys-$(CH_2)_3$-Glu2C$_{16}$ (6)

$NH_2$—$(CH_2)_3$—COOH (5.00 g, 48.5 mmol), $(BOC)_2O$ (11.6 g, 53.4 mmol) and triethylamine (5.39 g, 53.4 mmol) were dissolved in 200 mL of methanol, and the mixture was stirred at 60° C. for 12 hours. After the reaction completed, methanol was removed under reduced pressure, and the obtained material was redissolved in 100 mL of ethyl acetate. Then, the resultant solution was subjected to separation using 0.2 mol/l HCl (twice) and water (twice), and dehydrating was carried out with anhydrous sodium sulfate. After that, recrystallization with hexane at 4° C. and collection using a glass filter (G6) were performed, thereby obtaining Boc-NH—$(CH_2)_3$—COOH (6.98 g, 34.4 mmol, yield: 71%).

Boc-NH—$(CH_2)_3$—COOH (0.751 g, 3.70 mmol) and BOP (1.96 g, 4.07 mmol) were dissolved in 100 mL of dichloromethane, and the mixture was stirred at room temperature for 1 hour. After that, diacylglutamic acid derivative (1, 2.00 g, 3.36 mmol) and triethylamine (373 mg, 3.70 mmol) were added to the mixture and stirred for another 12 hours. After the reaction completed, the resultant solution was subjected to separation using a saturated aqueous solution of sodium carbonate (twice) and water (twice), and dehydrating was carried out with anhydrous sodium sulfate. After that, recrystallization with methanol at 4° C. and collection using a glass filter (G6) were performed. The purified product was collected, and the solvent was removed. After that, 5 mL of trifluoroacetic acid was added to the obtained material and stirred at 4° C. for 2 hours. After the reaction completed, the resultant solution was subjected to separation using a saturated aqueous solution of sodium carbonate (twice) and water (twice), and dehydrating was carried out with anhydrous sodium sulfate, thereby obtaining $NH_2$—$(CH_2)_3$-Glu2C$_{16}$ (1.33 g, 1.95 mmol, yield: 58%).

$NH_2$—$(CH_2)_3$-Glu2C$_{16}$ (1.00 g, 1.47 mmol), Boc-Lys(Boc)OSu (719 mg, 1.62 mmol) and triethylamine (164 mg, 1.62 mmol) were dissolved in 100 mL of dichloromethane, and then the mixture was stirred at room temperature for 12 hours. After the reaction completed, the resultant solution was subjected to separation using a saturated aqueous solution of sodium carbonate (twice) and water (twice), and dehydrating was carried out with anhydrous sodium sulfate. After that, recrystallization with methanol at 4° C. and collection using a glass filter (G6) were performed. The purified product was collected, and the solvent was removed. After that, 5 mL of trifluoroacetic acid was added to the obtained material and stirred at 4° C. for 2 hours. After the reaction completed, the resultant solution was subjected to separation using a saturated aqueous solution of sodium carbonate (twice) and water (twice), and dehydrating was carried out with anhydrous sodium sulfate, thereby obtaining a cationic lipid 6 (680 mg, 0.838 mmol, yield: 57%).

The analytical results of the cationic lipid 6 were as follows:

$^1$H-NMR (CDCl$_3$, 500 MHz, δ ppm): 0.88 (t, 6H, CH$_2$CH$_3$); 1.20-1.34 (br, 54H, CH$_2$), 1.42-1.52 (m, 2H, NHCH$_2$CH$_2$CH$_2$CO), 1.54-1.71 (m, 6H, OCOCH$_2$CH$_2$, NH$_2$CH$_2$CH$_2$) 1.76-1.86 (m, 2H, NH$_2$CH(CO)CH$_2$), 1.98-2.13 (m, 2H, CONHCHCH$_2$), 2.28 (t, 2H, NHCOCH$_2$), 2.35-2.47 (m, 2H, CH$_2$COO), 2.92 (t, 2H, NH$_2$CH$_2$), 3.25-3.30 (m, 2H, CONHCH$_2$), 3.43-3.47 (m, 1H, NH$_2$CH), 4.05-4.12 (m, 4H, COOCH$_2$), 4.50-4.57 (m, 1H, CONHCH), 7.36 (d, 1H, CHNH), 7.82 (t, 1H, CH$_2$NH). MS (ESI): (M+H)$^+$ calcd. for C$_{47}$H$_{92}$N$_4$O$_6$, 809.7; found, 809.9.

(B) Method for synthesizing Lys-$(CH_2)_5$-Glu2C$_{16}$ (5)

$NH_2$—$(CH_2)_5$—COOH (5.00 g, 38.2 mmol), $(BOC)_2O$ (9.16 g, 42.0 mmol) and triethylamine (4.24 g, 42.0 mmol) were dissolved in 200 mL of methanol, and the mixture was stirred at 60° C. for 12 hours. After the reaction completed, methanol was removed under reduced pressure, and the obtained material was redissolved in 100 mL of ethyl acetate. Then, the solution was subjected to separation using 0.2 mol/l HCl (twice) and water (twice), and dehydrating was carried out with anhydrous sodium sulfate. After that, recrystallization with hexane at 4° C. and collection using a glass filter (G6) were performed, thereby obtaining Boc-NH—$(CH_2)_5$—COOH (6.35 g, 27.5 mmol, yield: 72%).

Boc-NH—(CH$_2$)$_5$—COOH (0.855 g, 3.70 mmol) and BOP (1.96 g, 4.07 mmol) were dissolved in 100 mL of dichloromethane, and the mixture was stirred at room temperature for 1 hour. After that, diacylglutamic acid derivative (1, 2.00 g, 3.36 mmol) and triethylamine (373 mg, 3.70 mmol) were added to the mixture and stirred for another 12 hours. After the reaction completed, the resultant solution was subjected to separation using a saturated aqueous solution of sodium carbonate (twice) and water (twice), and dehydrating was carried out with anhydrous sodium sulfate. After that, recrystallization with methanol at 4° C. and collection using a glass filter (G6) were performed. The purified product was collected, and the solvent was removed. After that, 5 mL of trifluoroacetic acid was added to the obtained material and stirred at 4° C. for 2 hours. After the reaction completed, the resultant solution was subjected to separation using a saturated aqueous solution of sodium carbonate (twice) and water (twice), and dehydrating was carried out with anhydrous sodium sulfate, thereby obtaining NH$_2$—(CH$_2$)$_5$-Glu2C$_{16}$ (1.13 g, 1.61 mmol, yield: 48%).

NH$_2$—(CH$_2$)$_5$-Glu2C$_{16}$ (1 g, 1.42 mmol), Boc-Lys(Boc)OSu (693 mg, 1.56 mmol) and triethylamine (158 mg, 1.56 mmol) were dissolved in 100 mL of dichloromethane, and then the mixture was stirred at room temperature for 12 hours. After the reaction completed, the resultant solution was subjected to separation using a saturated aqueous solution of sodium carbonate (twice) and water (twice), and dehydrating was carried out with anhydrous sodium sulfate. After that, recrystallization with methanol at 4° C. and collection using a glass filter (G6) were performed. The purified product was collected, and the solvent was removed. After that, 5 mL of trifluoroacetic acid was added to the obtained material and stirred at 4° C. for 2 hours. After the reaction completed, the resultant solution was subjected to separation using a saturated aqueous solution of sodium carbonate (twice) and water (twice), and dehydrating was carried out with anhydrous sodium sulfate, thereby obtaining a cationic lipid 5 (419 mg, 0.497 mmol, yield: 35%).

The analytical results of the cationic lipid 5 were as follows:

$^1$H-NMR (CDCl$_3$, 500 MHz, δ ppm): 0.88 (t, 6H, CH$_2$CH$_3$); 1.20-1.35 (br, 58H, CH$_2$), 1.40-1.51 (br, 4H, CONHCH$_2$CH$_2$, NH$_2$CH$_2$CH$_2$), 1.52-1.68 (m, 6H, OCOCH$_2$CH$_2$, NH$_2$CH(CO)CH$_2$), 1.81-1.99 (m, 2H, CONHCHCH$_2$), 2.13-2.25 (br, 2H, NHCOCH$_2$), 2.33-2.41 (m, 2H, CH$_2$COO), 2.90-2.98 (br, 2H, NH$_2$CH$_2$), 3.16-3.25 (br, 2H, CONHCH$_2$), 3.75-3.90 (m, 1H, NH$_2$CH), 4.02-4.13 (m, 4H, COOCH$_2$), 4.53-4.56 (m, 1H, CONHCH), 7.09 (d, 1H, CHNH), 8.19 (t, 1H, CH$_2$NH). MS (ESI): (M+H)$^+$ calcd. for C$_{49}$H$_{96}$N$_4$O$_6$, 837.7; found, 837.8.

(c) Method for synthesizing Lys-(CH$_2$)$_7$-Glu2C$_{16}$ (7)

NH$_2$—(CH$_2$)$_7$—COOH (5.00 g, 31.4 mmol), (BOC)$_2$O (7.52 g, 34.5 mmol) and triethylamine (3.48 g, 34.5 mmol) were dissolved in 200 mL of methanol, and the mixture was stirred at 60° C. for 12 hours. After the reaction completed, methanol was removed under reduced pressure, and the obtained material was redissolved in 100 mL of ethyl acetate. Then, the resultant solution was subjected to separation using 0.2 mol/l HCl (twice) and water (twice), and dehydrating was carried out with anhydrous sodium sulfate. After that, recrystallization with hexane at 4° C. and collection using a glass filter (G6) were performed, thereby obtaining Boc-NH—(CH$_2$)$_7$—COOH (5.93 g, 22.9 mmol, yield: 73%).

Boc-NH—(CH$_2$)$_7$—COOH (0.958 g, 3.70 mmol) and BOP (1.96 g, 4.07 mmol) were dissolved in 100 mL of dichloromethane, and the mixture was stirred at room temperature for 1 hour. After that, diacylglutamic acid derivative (1, 2.00 g, 3.36 mmol) and triethylamine (373 mg, 3.70 mmol) were added to the mixture and stirred for another 12 hours. After the reaction completed, the resultant solution was subjected to separation using a saturated aqueous solution of sodium carbonate (twice) and water (twice), and dehydrating was carried out with anhydrous sodium sulfate. After that, recrystallization with methanol at 4° C. and collection using a glass filter (G6) were performed. The purified product was collected, and the solvent was removed. After that, 5 mL of trifluoroacetic acid was added to the obtained material and stirred at 4° C. for 2 hours. After the reaction completed, the resultant solution was subjected to separation using a saturated aqueous solution of sodium carbonate (twice) and water (twice), and dehydrating was carried out with anhydrous sodium sulfate, thereby obtaining NH$_2$—(CH$_2$)$_7$-Glu2C$_{16}$ (1.37 g, 1.88 mmol, yield: 56%).

NH$_2$—(CH$_2$)$_7$-Glu2C$_{16}$ (1 g, 1.37 mmol), Boc-Lys(Boc)OSu (670 mg, 1.51 mmol) and triethylamine (153 mg, 1.51 mmol) were dissolved in 100 mL of dichloromethane, and then the mixture was stirred at room temperature for 12 hours. After the reaction completed, the resultant solution was subjected to separation using a saturated aqueous solution of sodium carbonate (twice) and water (twice), and dewatering was carried out with anhydrous sodium sulfate. After that, recrystallization with methanol at 4° C. and collection using a glass filter (G6) were performed. The purified product was collected, and the solvent was removed. After that, 5 mL of trifluoroacetic acid was added to the obtained material and stirred at 4° C. for 2 hours. After the reaction completed, the resultant solution was subjected to separation using a saturated aqueous solution of sodium carbonate (twice) and water (twice), and dewatering was carried out with anhydrous sodium sulfate, thereby obtaining a cationic lipid 7 (534 mg, 0.617 mmol, yield: 45%).

The analytical results of the cationic lipid 7 were as follows:

$^1$H-NMR (CDCl$_3$, 500 MHz, δ ppm): 0.88 (t, 6H, CH$_2$CH$_3$); 1.14-1.34 (br, 60H, CH$_2$), 1.40-1.52 (br, 2H, NHCOCH$_2$CH$_2$) 1.54-1.70 (m, 8H, OCOCH$_2$CH$_2$, NH$_2$CH$_2$CH$_2$, CONHCH$_2$CH$_2$), 1.75-1.82 (m, 2H, NH$_2$CH(CO)CH$_2$), 1.92-2.24 (m, 2H, CONHCHCH$_2$), 2.21 (t, 2H, NHCOCH$_2$), 2.30-2.46 (m, 2H, CH$_2$COO), 2.85 (t, 2H, NH$_2$CH$_2$), 3.16-3.24 (m, 2H, CONHCH$_2$), 3.34-3.76 (m, 1H, NH$_2$CH), 4.02-4.15 (m, 4H, COOCH$_2$), 4.57-4.61 (m, 1H, CONHCH), 6.47 (d, 1H, CHNH), 7.52 (t, 1H, CH$_2$NH). MS (ESI): (M+H)$^+$ calcd. for C$_{51}$H$_{100}$N$_4$O$_6$, 865.8; found, 866.1.

(D) Method for synthesizing Lys-(CH$_2$)$_{11}$-Glu2C$_{16}$ (8)

NH$_2$—(CH$_2$)$_{11}$—COOH (5.00 g, 23.3 mmol), (Boc)$_2$O (5.58 g, 25.6 mmol) and triethylamine (2.59 g, 25.6 mmol) were dissolved in 200 mL of methanol, and the mixture was stirred at 60° C. for 12 hours. After the reaction completed, methanol was removed under reduced pressure, and the obtained material was redissolved in 100 mL of ethyl acetate. Then, the resultant solution was subjected to separation using 0.2 mol/l HCl (twice) and water (twice), and dehydrating was carried out with anhydrous sodium sulfate. After that, recrystallization with hexane at 4° C. and collection using a glass filter (G6) were performed, thereby obtaining Boc-NH—(CH$_2$)$_{11}$—COOH (6.17 g, 19.6 mmol, yield: 84%).

Boc-NH—(CH$_2$)$_{11}$—COOH (1.17 g, 3.70 mmol) and BOP (1.96 g, 4.07 mmol) were dissolved in 100 mL of dichloromethane, and the mixture was stirred at room temperature for 1 hour. After that, diacylglutamic acid derivative (1, 2.00 g, 3.3.6 mmol) and triethylamine (373 mg, 3.70 mmol) were added to the mixture and stirred for another 12 hours. After the reaction completed, the resultant solution was subjected to separation using a saturated aqueous solution of sodium carbonate (twice) and water (twice), and dehydrating was carried out with anhydrous sodium sulfate. After that, recrystallization with methanol at 4° C. and collection using a glass filter (G6) were performed. The purified product was collected, and the solvent was removed. After that, 5 mL of trifluoroacetic acid was added to the obtained material and stirred at 4° C. for 2 hours. After the reaction completed, the resultant solution was subjected to separation using a saturated aqueous solution of sodium carbonate (twice) and water (twice), and dehydrating was carried out with anhydrous sodium sulfate, thereby obtaining NH$_2$—(CH$_2$)$_{11}$-Glu2C$_{16}$ (1.09 g, 1.41 mmol, yield: 42%).

NH$_2$—(CH$_2$)$_{11}$-Glu2C$_{16}$ (1.00 g, 1.29 mmol), Boc-Lys (Boc)OSu (630 mg, 1.42 mmol) and triethylamine (143 mg, 1.42 mmol) were dissolved in 100 mL of dichloromethane, and then the mixture was stirred at room temperature for 12 hours. After the reaction completed, the resultant solution was subjected to separation using a saturated aqueous solution of sodium carbonate (twice) and water (twice), and dehydrating was carried out with anhydrous sodium sulfate. After that, recrystallization with methanol at 4° C. and collection using a glass filter (G6) were performed. The purified product was collected, and the solvent was removed. After that, 5 mL of trifluoroacetic acid was added to the obtained material and stirred at 4° C. for 2 hours. After the reaction completed, the resultant solution was subjected to separation using a saturated aqueous solution of sodium carbonate (twice) and water (twice), and dewatering was carried out with anhydrous sodium sulfate, thereby obtaining a cationic lipid 8 (617 mg, 0.670 mmol, yield: 54%).

The analytical results of the cationic lipid 8 were as follows:

$^1$H-NMR (CDCl$_3$, 500 MHz, δ ppm): 0.88 (t, 6H, CH$_2$CH$_3$); 1.14-1.34 (br, 68H, CH$_2$), 1.40-1.52 (br, 2H, NHCOCH$_2$CH$_2$) 1.52-1.71 (m, 8H, OCOCH$_2$CH$_2$, NH$_2$CH$_2$CH$_2$, CONHCH$_2$CH$_2$), 1.78-1.86 (m, 2H, NH$_2$CH (CO)CH$_2$), 1.94-2.24 (m, 2H, CONHCHCH$_2$), 2.21 (t, 2H, NHCOCH$_2$), 2.30-2.46 (m, 2H, CH$_2$COO), 2.80 (t, 2H, NH$_2$CH$_2$), 3.10-3.24 (m, 2H, CONHCH$_2$), 3.33-3.40 (m, 1H, NH$_2$CH), 4.02-4.14 (m, 4H, COOCH$_2$), 4.58-4.62 (m, 1H, CONHCH), 7.60 (d, 1H, CHNH), 8.21 (t, 1H, CH$_2$NH). MS (ESI): (M+H)$^+$ calcd. for C$_{55}$H$_{108}$N$_4$O$_6$, 1026.8; found, 1026.9.

Example 13

Method for Synthesizing Lys-PEG-DHSG (Compound 9)

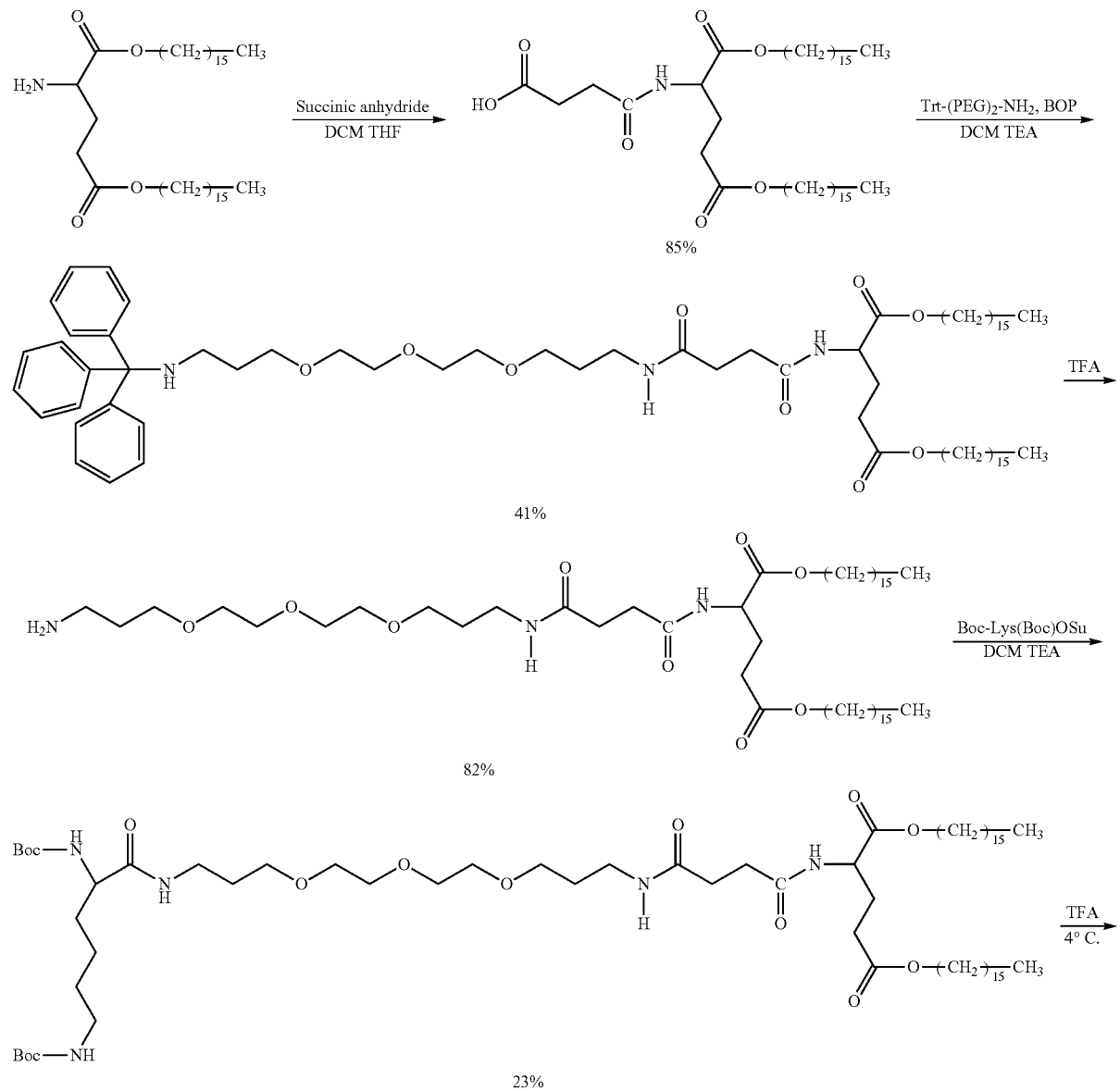

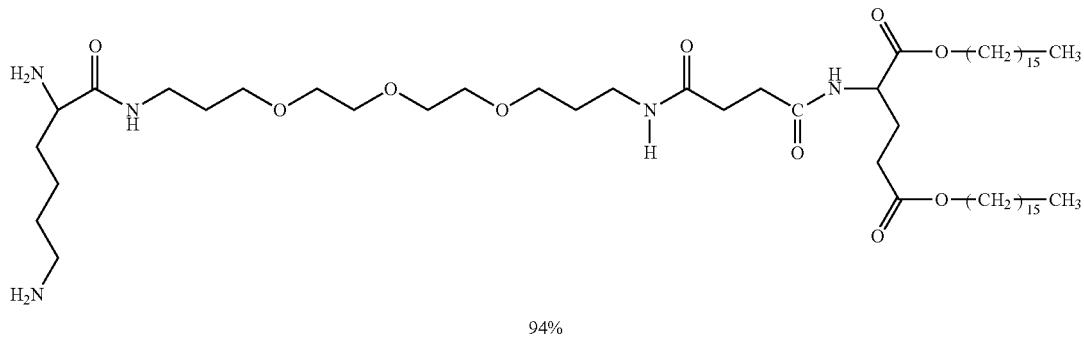

compound 9

94%

As shown in the above-described scheme, synthesis of Compound 9 was carried out. Hereinafter, the method for synthesizing the lipid will be specifically described.

Diacylglutamic acid derivative (3.5 g, 5.87 mmol) and succinic anhydride (0.88 g, 8.81 mmol) were dissolved in 25 mL of dichloromethane and 25 mL of tetrahydrofuran, and the mixture was stirred at room temperature for 12 hours. After the reaction completed, the reaction solution was added dropwise to 300 mL of acetone, and the mixture was subjected to recrystallization at 4° C., filtration and drying, thereby obtaining DHSG (3.47 g, 4.99 mmol, yield: 85%).

DHSG (1.66 g, 2.39 mmol) and BOP (1.12 g, 2.82 mmol) were dissolved in 100 mL of dichloromethane, and the mixture was stirred at room temperature for 1 hour. After that, Trt-(PEG)$_2$-NH$_2$ (1.0 g, 2.16 mmol) and triethylamine (0.24 mg, 2.37 mmol) were added to the mixture and stirred for another 12 hours. After the reaction completed, the resultant mixture was purified using a column (chloroform/methanol=20/1). 5 mL of trifluoroacetic acid was added to the purified product and stirred at 4° C. for 2 hours. After the reaction completed, the solvent was distilled away under reduced pressure, and purification was carried out using a column (chloroform/methanol=5/1), thereby obtaining NH$_2$-(PEG)$_2$-DHSG (0.66 g, 0.73 mmol, yield: 34%).

NH$_2$-(PEG)$_2$-DHSG (0.50 g, 0.56 mmol), Boc-Lys(Boc)OSu (0.28 g, 0.62 mmol) and triethylamine (0.063 g, 0.62 mmol) were dissolved in 50 mL of dichloromethane, and then the mixture was stirred at room temperature for 12 hours. After the reaction completed, purification was performed using a column (chloroform/methanol=20/1). To the purified product, 5 mL of trifluoroacetic acid was added and stirred at 4° C. for 2 hours. After the reaction completed, the solvent was distilled away under reduced pressure, and diethylether was added. Crystal precipitated was collected using a glass filter (G6). The collected crystal was allowed to stand in a desiccator in which NaOH was spread for 5 hours to obtain Compound 9 (Lys-PEG-DHSG) (0.23 mg, 0.22 mmol, yield: 39%).

The analytical results of Compound 9 were as follows:

$^1$H-NMR (CDCl$_3$/MeOD=4/1, 500 MHz, δ ppm): 0.88 (t, 6H, CH$_2$CH$_3$); 1.14-1.34 (br, 52H, CH$_2$), 1.46-1.52 (br, 2H, CHCH$_2$CH$_2$) 1.58-1.66 (m, 4H, OCOCH$_2$CH$_2$), 1.69-1.81 (m, 6H, NH$_2$CH(CO)CH$_2$, CONHCH$_2$CH$_2$), 1.82-1.89 (m, 2H, NH$_2$CH$_2$CH$_2$), 1.93-2.19 (m, 2H, CONHCHCH$_2$), 2.33-2.41 (m, 2H, CH$_2$COO), 2.45-2.55 (m, 2H, NHCOCH$_2$), 2.96 (t, 2H, NH$_2$CH$_2$), 3.25-3.34 (m, 4H, CONHCH$_2$), 3.50-3.65 (br, 12H, OCH$_2$), 3.88-3.92 (m, 1H, NH$_2$CH), 4.02-4.15 (m, 4H, COOCH$_2$), 4.46-4.51 (m, 1H, CONHCH), 6.27 (d, 1H, CHNH), 7.35 (t, 1H, CH$_2$NH). MS (ESI): (M+H)$^+$ calcd. for C$_{51}$H$_{100}$N$_4$O$_6$, 922.1; found, 921.8.

Example 14

Preparation of Liposomes

Each of the cationic lipids, etc. synthesized in Examples 12 and 13 was mixed with dioleylphosphatidylcholine (DOPC), cholesterol (chol) and PEG-Glu2C$_{18}$ at a corresponding molar ratio described in Table 6 below, and then the mixture was dissolved in tert-butylalcohol. The obtained solution was freeze-dried to prepare a mixed lipid. 30 mg of the prepared mixed lipid was hydrated with 1.5 mL of HEPES buffer solution (pH 7.4) for 6 hours, and the extrusion method (final pore size: 0.22 μm) was applied to the resultant mixture to prepare liposomes having the particle size of about 250 nm.

TABLE 6

| | Lipids composition | |
|---|---|---|
| | Lipid components | Molar ratio |
| I | a/DOPC/Chol/PEG-Glu2C18 | |
| II | b/DOPC/Chol/PEG-Glu2C18 | |
| III | c/DOPC/Chol/PEG-Glu2C18 | |
| IV | d/DOPC/Chol/PEG-Glu2C18 | 1/5/5/0.033 |
| V | e/DOPC/Chol/PEG-Glu2C18 | 5/5/0.033 |
| VI | f/DOPC/Chol/PEG-Glu2C18 | |
| VII | DOTMA/DOPC/Chol/PEG-Glu2C18 | |
| VIII | DOPC/Chol/PEG-Glu2C18 | |

*In the table above, a to f represent Compounds (amino acid type cationic lipids) 2, 6, 5, 7, 8 and 9, respectively.

compound 2

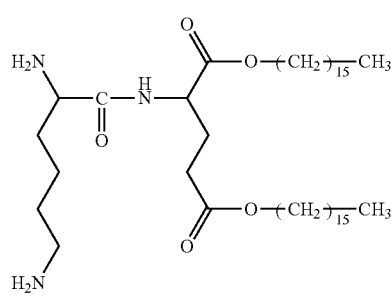

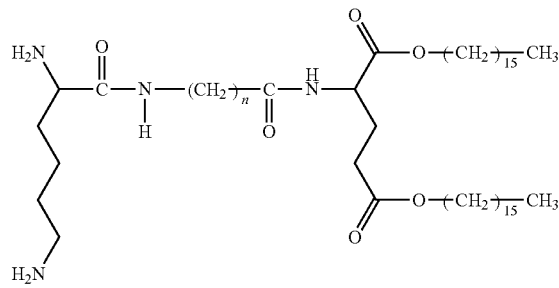

n = 3 compound 6
n = 5 compound 5
n = 7 compound 7
n = 11 compound 8 compound 9

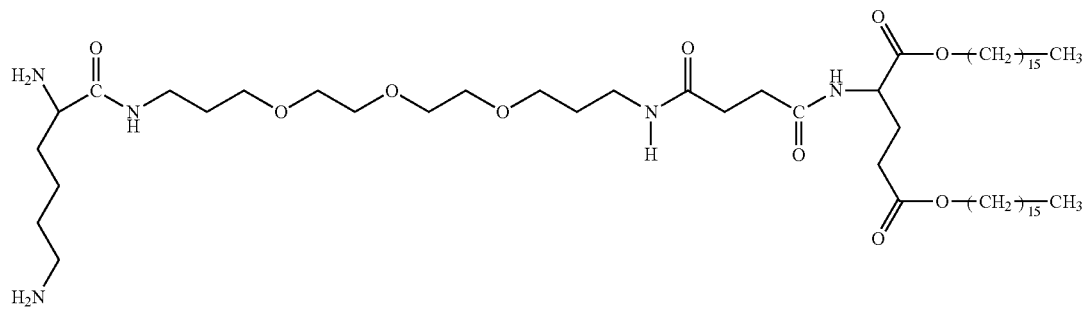

Physical Properties of Liposomes

The particle size and the ζ potential of the prepared cationic liposomes were measured. In the measurement of the particle size, the particle size in the case of the lipid concentration of 30 μM was measured by the dynamic light scattering method. In the measurement of the ζ potential, a liposome dispersion was diluted with a HEPES buffer solution (pH 7.4), and the ζ potential in the case of 30 μM was measured. The results are shown in Table 7.

the ζ potential is caused by introduction of spacer and is associated with the length and type of spacer.

Next, the fusion degree of each of the prepared cationic liposomes to biomembrane was measured. As a biomembrane model, into a liposome consisting of DOPC/DOPS/chol (molar ratio: 3/0.3/1), fluorescent lipids NBD-PE and Rho-PE were introduced, and the fusion ratio was calculated based on the disappearance degree of FRET. 100 mM biomembrane model liposome and 100 mM cationic lipo-

TABLE 7

Characteristics of cationic liposomes embedded spacer modified lipids.

| | Lipid components | Spacer-type | Molar ratio | Diameter [nm] | Zeta-potential [mV] |
|---|---|---|---|---|---|
| I | A/DOPC/Chol | No spacer | 1/5/5 | 268 ± 111 | 2.4 |
| II | B/DOPC/Chol | Alkyl (n = 3) | 1/5/5 | 288 ± 119 | 4.0 |
| III | C/DOPC/Chol | Alkyl (n = 5) | 1/5/5 | 285 ± 112 | 10.6 |
| IV | D/DOPC/Chol | Alkyl (n = 7) | 1/5/5 | 275 ± 111 | 6.5 |
| V | E/DOPC/Chol | Alkyl (n = 11) | 1/5/5 | 333 ± 133 | 0.5 |
| VI | F/DOPC/Chol | PEG | 1/5/5 | 266 ± 105 | 12.3 |
| VII | DOTMA/DOPC/Chol | — | 1/5/5 | 276 ± 93 | 14.6 |
| VIII | DOPC/Chol | — | 5/5 | 308 ± 135 | −1.7 |

PEG lipid: 0.3 mol %
* In the table above, A to F represent Compounds (amino acid type cationic lipids) 2, 6, 5, 7, 8 and 9, respectively.

When the cationic lipid 2 which has no spacer was used as a liposome membrane component (I), the ζ potential was +2.4 mV. Meanwhile, when an alkyl group was introduced as a spacer, the ζ potential was increased (II to V). When increase in the alkyl chain length was 0→6→5, the ζ potential was increased, but when the increase was 5→7→11, the ζ potential was decreased. Next, when a polyoxyethylene-type spacer was introduced, the highest ζ potential was obtained (VI). When DOTMA, which is widely used as a gene carrier, was utilized by way of comparison, the ζ potential of the liposome was 14.6 mV (VII). It became clear that change in some were mixed together at 37° C., and the fusion ratio was calculated based on the fluorescence intensity 5 minutes later (excitation: 460 nm, fluorescence: 534 nm) and the fluorescence intensity obtained when 0.1% Triton-X was added. The results are shown in FIG. 7.

Figure 7:
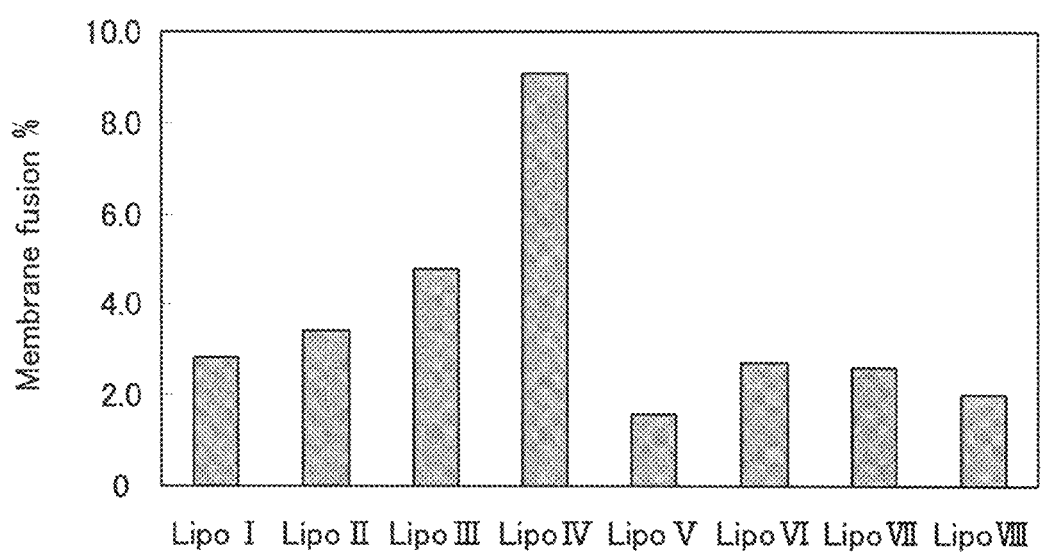
FIG. 7 is a graph showing measurement results regarding the fusion degree of cationic liposomes to biomembrane.

As shown in FIG. 7, the cationic lipid with an alkyl-type spacer having 7 carbon atoms showed the highest fusion degree (IV). Meanwhile, the liposome consisting of the cationic lipid into which a polyoxyethylene-type spacer was introduced had a high ζ potential, but the fusion degree thereof was low (VI).

Example 15

Preparation of pDNA-Encapsulated Liposome

An attempt to encapsulate pDNA (4045 bp) into each of the cationic liposomes, etc. prepared in Examples 12 and 13 was made (see the below scheme A). A mixed lipid was dissolved in 90 vol % ethanol (1 mL), and with the equal amount of 20 mM PB buffer solution (pH 5), the dispersed pDNA was mixed. Next, 2 mL of 300 mM NaCl was added dropwise thereto with stirring, and stirring and mixing were further performed for 1 hour. After that, pDNA which electrostatically bound to the liposome surface was removed by means of anion-exchange chromatography. Ultracentrifugation (1,600,000×g) was performed, and then redispersion was performed with PBS. Physical properties of the prepared pDNA-encapsulated liposomes are shown in Table 8.

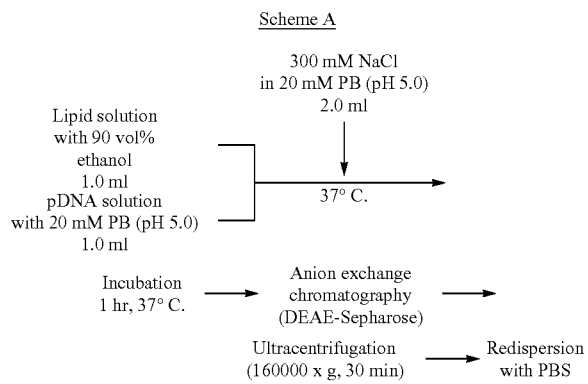

Scheme A

Confirmation of Encapsulation of pDNA by Gel Electrophoresis

Figure 9:
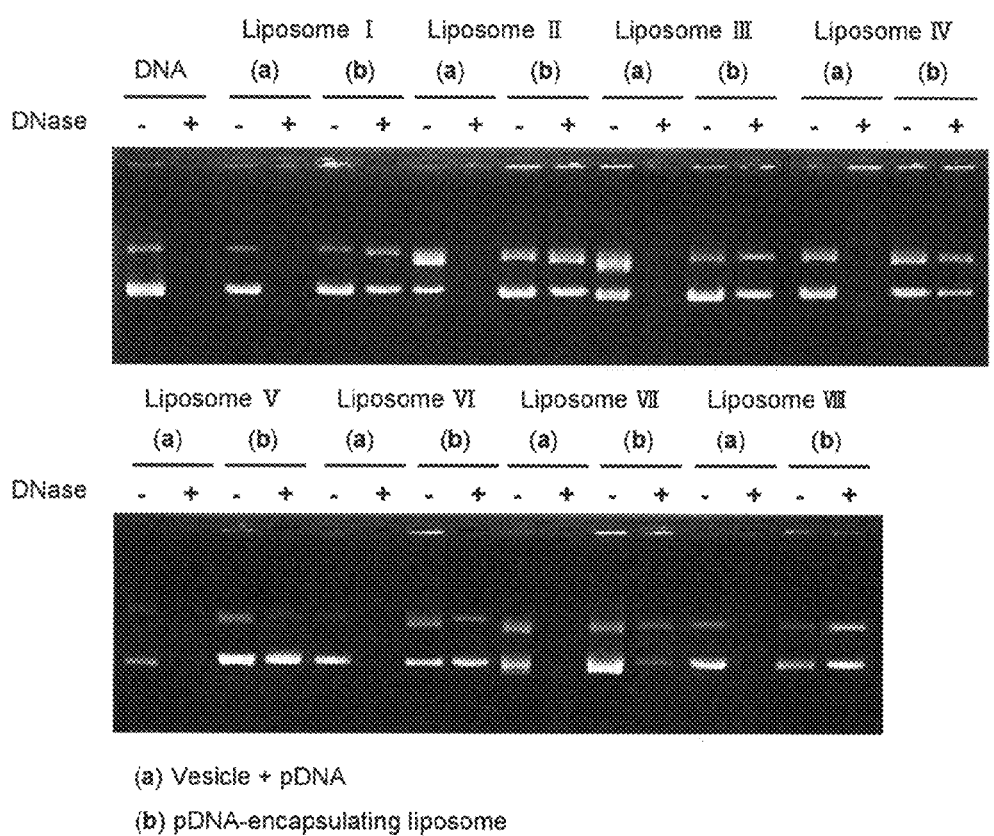
FIG. 9 shows confirmation results regarding encapsulation of pDNA in the cationic liposomes obtained by gel electrophoresis.

Encapsulation of pDNA in the cationic liposomes was confirmed by gel electrophoresis. Each of the pDNA-encapsulated liposomes was mixed with DNase, and the mixture was incubated at 37° C. for 1 hour. After that, pDNA was extracted with chloroform, and electrophoresis was performed for 1 hour using 1% agarose gel. The results are shown in FIG. 9.

In the case of pDNA alone and the case of the complex of the cationic liposomes and pDNA, degradation caused by DNase was observed. In the case of the pDNA-encapsulated liposomes, the bands of pDNA were observed even when DNase was added, and therefore, it was confirmed that pDNA was encapsulated.

Gene Expression Efficiency

The gene expression efficiency of each of the pDNA-encapsulated liposomes was calculated. $1 \times 10^4$ COS-1 cells were seeded on a 96-well plate, and 12 hours later, the pDNA-encapsulated liposome was added thereto with the pDNA concentration of 2 μg/mL. 72 hours later, it was washed with PBS twice and the cells were solubilized. 100 μL of luciferin was added to 20 μL of the solubilized solution, and the luminescence intensity (RLU) thereof was measured. Further, the protein concentration of 5 μL of cell-solubilized solution was measured, and based thereon, the gene expression efficiency (RLU/Protein) was calculated. The results are shown in FIG. 10.

Figure 10:
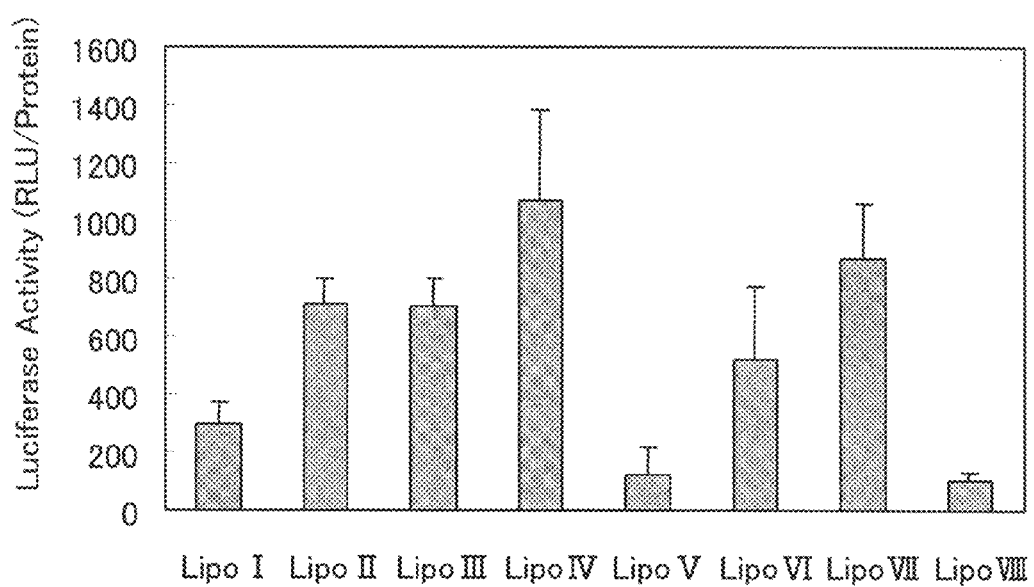
FIG. 10 is a graph showing calculation results regarding gene expression efficiency of pDNA-encapsulated liposomes.

As shown in FIG. 10, Liposome IV showed the highest gene expression efficiency. When the chain length of the alkyl spacer was increased from 0 to 7, higher gene expression was obtained. However, when the alkyl chain length was increased to 11, the gene expression efficiency was significantly reduced. When using a polyoxyethylene-type spacer (Liposome VI), the ζ potential was high, but the gene expres-

TABLE 8

Characteristics of pDNA-encapsulating cationic liposomes.

| | Lipid components | Spacer | Molar ratio | Diameter [nm] | Encapsulation ratio [%] |
|---|---|---|---|---|---|
| I | A/DOPC/Chol | No spacer | 1/5/5 | 174 ± 66 | 38 |
| II | B/DOPC/Chol | Alkyl (n = 3) | 1/5/5 | 248 ± 99 | 30 |
| III | C/DOPC/Chol | Alkyl (n = 5) | 1/5/5 | 186 ± 69 | 49 |
| IV | D/DOPC/Chol | Alkyl (n = 7) | 1/5/5 | 229 ± 91 | 39 |
| V | E/DOPC/Chol | Alkyl (n = 11) | 1/5/5 | 236 ± 104 | 30 |
| VI | F/DOPC/Chol | PEG | 1/5/5 | 203 ± 78 | 33 |
| VII | DOTMA/DOPC/Chol | — | 1/5/5 | 159 ± 63 | 33 |
| VIII | DOPC/Chol | — | 5/5 | 198 ± 81 | 10 |

PEG lipid: 0.3 mol %
* In the table above, A to F represent Compounds (amino acid type cationic lipids) 2, 6, 5, 7, 8 and 9, respectively.

Observation Using TEM

Each of the prepared pDNA-encapsulated liposomes was observed using TEM. 3 μL of the liposome dispersion with the lipid concentration of 700 μM was put on a copper grid and allowed to stand for 3 minutes. After that, excess water was absorbed using a filter paper, and 3 μL of aqueous solution of sodium phosphotungstate was added dropwise to the resultant material. After allowed to stand for 3 minutes, water was absorbed using a filter paper to provide a sample for measurement. The results of TEM observation are shown in FIG. 8.

Figure 8:
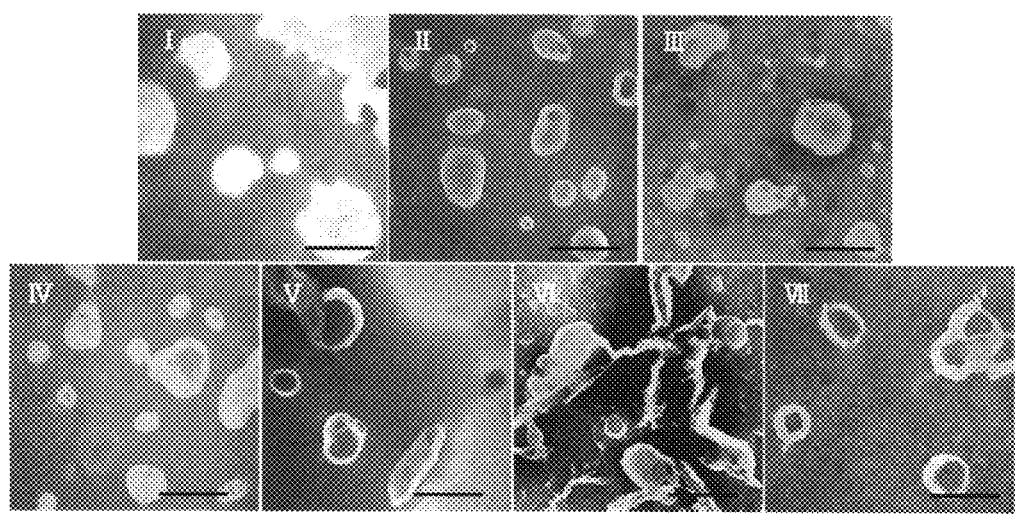
FIG. 8 shows images of pDNA-encapsulated liposomes observed by TEM.

As shown in FIG. 8, an aggregate having a vesicle structure was observed in all the liposomes except for Liposome VI. Meanwhile, in the case of Liposome VI, in addition to the vesicle structure, a tube-like structure was also observed.

sion was not so high. It is considered that gene expression is associated with the fusion ratio to cell membrane and the introduction efficiency.

Example 16

Study of Use of Cationic Lipid as Reagent for Gene Introduction

Use of a cationic lipid as a reagent for gene introduction was studied. Cationic liposomes consisting of a mixed membrane constituted by DOPE as a membrane-fusogenic lipid and a cationic lipid were prepared. 15 mg of the mixed lipid (the introduction amount of cationic lipid membrane in mixed membrane was adjusted to 20, 30, 40 or 50 mol %) was dispersed in 1.5 mL of the HEPES buffer solution (pH 7.4), and a liposome having the particle size of about 100 nm was prepared using a probe-type ultrasonic apparatus. The particle size was measured by the dynamic light scattering method. The results are shown in Table 9. In the table, A represents a cationic lipid 2 and a cationic lipid 6; B represents a cationic lipid 5; C represents a cationic lipid 7; and D represents a cationic lipid 8.

TABLE 9

|  | A | B | C | D |
|---|---|---|---|---|
| 20 mol % | 93 ± 41 | 99 ± 45 | 88 ± 42 | 95 ± 36 |
| 30 mol % | 89 ± 47 | 95 ± 46 | 98 ± 37 | 113 ± 50 |
| 40 mol % | 104 ± 47 | 91 ± 43 | 86 ± 40 | 80 ± 39 |
| 50 mol % | 113 ± 50 | 100 ± 47 | 100 ± 48 | 95 ± 36 |

Next, the $\zeta$ potential of the prepared cationic liposomes was measured. The results are shown in Table 10. A to D in the table was the same as Table 9.

TABLE 10

|  | A | B | C | D |
|---|---|---|---|---|
| 20 mol % | 30 ± 0.8 | 28 ± 3.4 | 34 ± 42 | 30 ± 1.2 |
| 30 mol % | 30 ± 0.4 | 37 ± 0.2 | 40 ± 3.3 | 37 ± 0.8 |
| 40 mol % | 33 ± 0.4 | 42 ± 3.0 | 49 ± 3.3 | 37 ± 3.1 |
| 50 mol % | 40 ± 1.0 | 41 ± 1.3 | 37 ± 3.1 | 44 ± 1.6 |

There was a tendency that the longer the spacer was, the higher the $\zeta$ potential was. However, the $\zeta$ potential of the spacer-contained lipid 8 was slightly lower than that of the lipid 7. When the respective membrane contents were compared to each other, there was a tendency that the more the content was, the higher the $\zeta$ potential was.

Quantification of Gene Expression Level

In order to evaluate the gene transfer ability of the prepared cationic liposomes, the gene expression level was calculated based on luciferase assay using an luciferase-encoding plasmid vector (phRL-TK) (n=3).

The experimental protocol was as follows. The amount of transfected DNA was set to 200 ng in all the cases. In 100 μL of medium, COS-1 cells ($1\times10^4$ cells/well) were seeded on a 96-well plate, and cultured in a $CO_2$ incubator for 12 hours. A complex of lipid and plasmid DNA (lipid/pDNA complex) was allowed to stand for minutes, and diluted with the medium to be added to the cells. After that, culture in the $CO_2$ incubator was carried out for 24 hours. The medium was removed, and washing with PBS(–) was carried out twice. Then, a dissolution buffer diluted 5-fold with MilliQ water was added to the medium (25 μl/well), and the cells were solubilized. The obtained solution was mildly stirred and allowed to stand at room temperature for minutes. To 20 μL of the cell solution, 100 μL of the coelenterazine solution was added, and the luminescence intensity was measured using a luminometer. The results are shown in FIG. 11.

Figure 11:
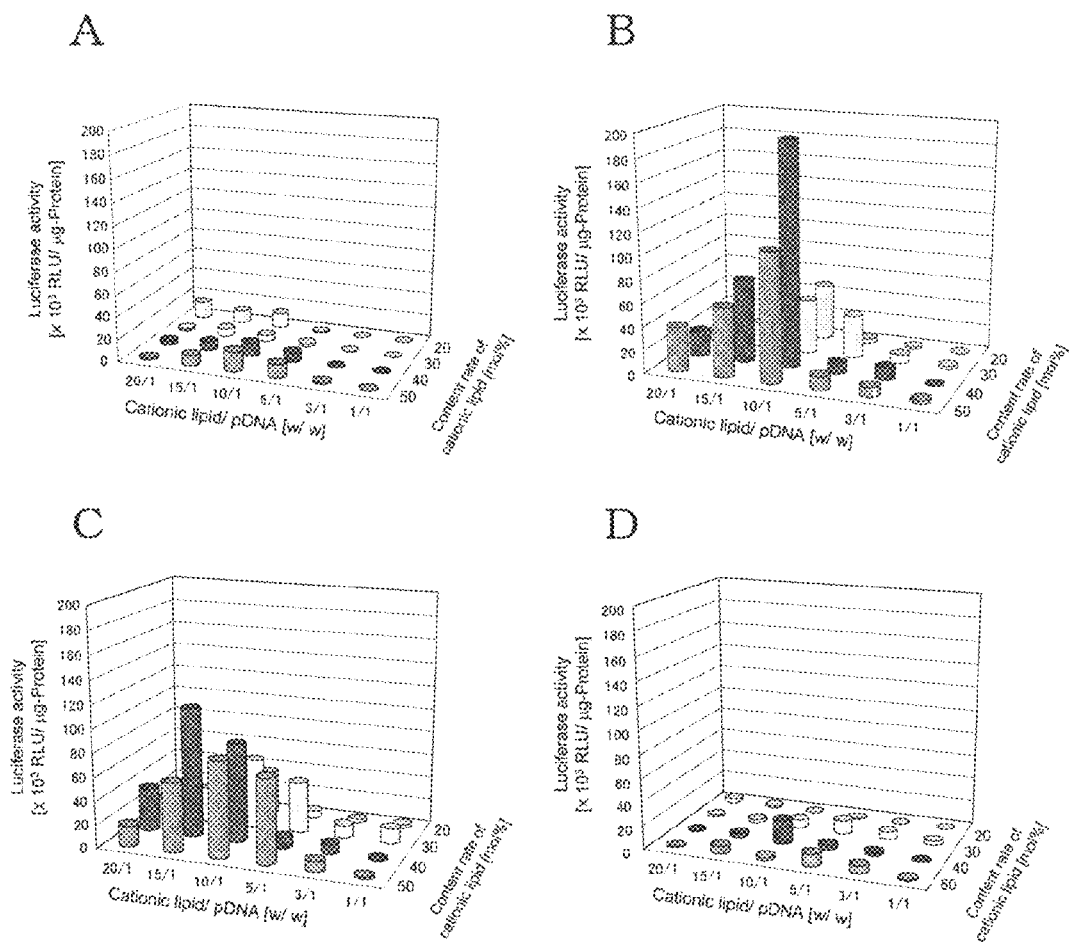
FIG. 11 shows graphs showing calculation results regarding the expression level based on luciferase assay, which are used for evaluating the gene transfer ability of the cationic liposomes.

As shown in FIG. 11, a high expression efficiency was obtained when using the spacer-contained lipid 6 as the membrane component (B in FIG. 11). The highest expression efficiency was obtained using the following conditions: the cationic liposome consisting of DOPE and the lipid 6 (DOPE/lipid 6=6/4 (mol ratio)); and the mixing ratio between the cationic liposome and the plasmid DNA of 10/1 (w/w). When using the lipid 2 into which no spacer was introduced or the spacer-contained lipid d as the membrane component, even when the membrane content, the mixing ratio, etc. were changed, the gene expression level was low (A and D in FIG. 11). In the case of the spacer-contained lipid 5, gene expression occurred, but the expression level was lower than that of the spacer-contained lipid 6. That is, it was suggested that the structure of spacer lipid in the liposome consisting of the mixed membrane with DOPE was 6.

INDUSTRIAL APPLICABILITY

The present invention provides a reagent for introducing a protein or gene into a cell, which comprises a composition comprising a complex lipid having a cationic functional group derived from an amino acid.

Attention is focused on the technique to introduce a protein or gene from outside into a cell to transform the cell, and it is expected to be applied to biotechnology, cellular therapy, etc. In the case of protein introduction, a protein introduced is not continuously replicated. However, if a protein which exerts sufficient functions even in transient expression is targeted, the present invention will be a significantly useful technique.

The cationic amino acid type lipid to be used in the present invention can be synthesized inexpensively and in large quantity because of easiness of procurement of raw materials and synthesis thereof. The cationic lipid to be used in the present invention is used as a composition constituted by a single compound or a plurality of compounds. The composition may be in the miscible state and amorphous. According to a preferred embodiment of the present invention, the composition may be used as a constituent in a molecular assembly which is dispersed in an aqueous medium such as micelles, lipid microspheres, liposomes, etc., and the dispersion of the molecular assembly may be dried. According to this embodiment, affinity to cells can be improved, and a reagent having a significantly high intracellular migration capability can be obtained.

Further, among the cationic amino acid type lipids to be used in the present invention, a lysine-type lipid (amino acid type lipid) has high liposome forming ability, and therefore a protein or gene can be stably encapsulated therein.

In the case of the lysine-type lipid, an amino group present at the side chain of the lysine residue is more positively charged under low pH environment within an endosome. Therefore, there is a possibility of occurrence of the proton sponge effect within the endosome or fusion with an endosome membrane which is anionically charged like 1,2-dioleoyl-sn-glycero-3-phosphoethanolamine (DOPE). In the case of gene introduction, it has become clear that, even if DOPE is not mixed, high gene expression efficiency is actually obtained only by performing complexation of a plasmid DNA using a lysine-type lipid solely. Further, the gene introduction system using the lysine-type lipid is characterized in that the gene expression efficiency in serum is not reduced.

Moreover, the aforementioned amino acid type lipid has high biodegradability, and since a degraded product is an amino acid, a derivative thereof, long-chain alcohol or the like, it has low toxicity.

Therefore, the reagent of the present invention is significantly useful for introducing a protein or gene into a cell.

The invention claimed is:

1. A reagent for introducing a protein into a cell, which comprises a composition comprising a cationic amino acid type lipid represented by the following formula (I)-1:

1.

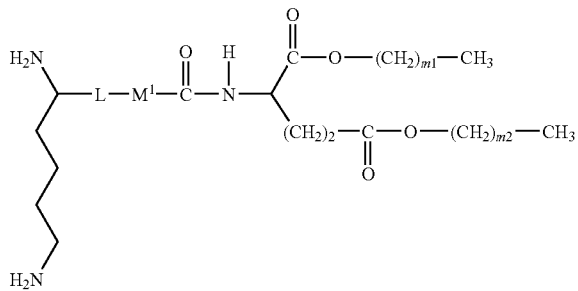

wherein: L is a single bond, —CONH—, or —S—S—; $M^1$ is —$(CH_2)_k$— or —$(CH_2CH_2O)_k$—; k is an integer between 1 and 11; and m1 and m2 are each independently an integer between 11 and 21.

2. A reagent for introducing a gene into a cell, which comprises a composition comprising a cationic amino acid type lipid represented by the following formula (I)-1:

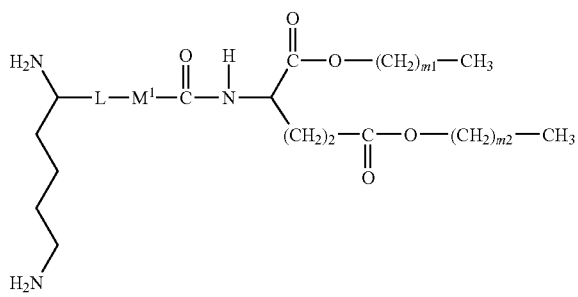

wherein: L is a single bond, —CONH—, or —S—S—; $M^1$ is —$(CH_2)_k$— or —$(CH_2CH_2O)_k$—; k is an integer between 1 and 11; and m1 and m2 are each independently an integer between 11 and 21; with the proviso that both m1 and m2 are not an integer of 15.

3. The reagent according to claim 1 or 2, wherein the composition further comprises at least one substance selected from the group consisting of diacylphosphatidylcholine, cholesterol, and an amphipathic molecule to which a polyethylene glycol chain is bound.

4. The reagent according to claim 3, wherein one or two acyl chains of diacylphosphatidylcholine is an oleoyl group.

5. The reagent according to claim 1 or 2, wherein the composition is a molecular assembly dispersed in an aqueous medium.

6. The reagent according to claim 5, wherein the molecular assembly forms a bilayer membrane vesicle structure, and wherein an inner aqueous phase thereof includes a protein or gene.

7. The reagent according to claim 1 or 2, wherein the composition is a dry powder product.

8. The reagent according to claim 7, wherein the dry powder product can form a bilayer membrane vesicle structure including a protein or gene when dispersed in an aqueous medium.

9. The reagent according to claim 1 or 2, wherein the cell is: a cell constituting a part of body tissue; plasma, serum or blood; or a cell cultured in a medium containing a part of components thereof.

10. A kit for introducing a protein or gene into a cell, which comprises the reagent according to claim 1 or 2.

11. A cationic amino acid type lipid represented by the following formula (I)-3:

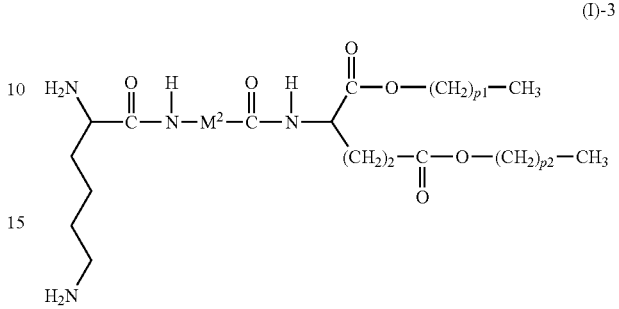

wherein: $M^2$ is —$(CH_2)_{k'}$— or —$(CH_2CH_2O)_{k'}$—; k' is an integer between 1 and 14; and p1 and p2 are each independently an integer between 11 and 21.

12. A reagent for introducing a protein into a cell, which comprises a composition comprising a cationic amino acid type lipid represented by the following formula (I)-1:

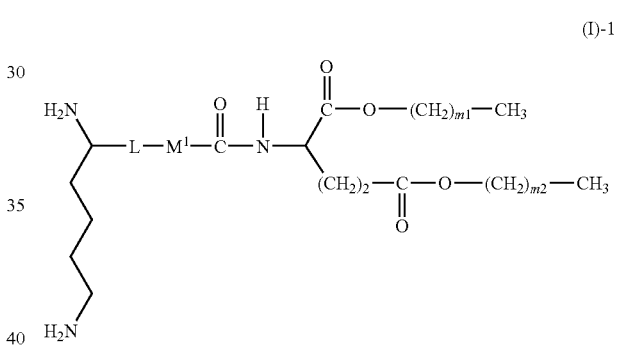

wherein: L is —CONH—, or —S—S—; $M^1$ is —$(CH_2)_k$— or —$(CH_2CH_2O)_k$—; k is an integer between 2 and 14; and m1 and m2 are each independently an integer between 11 and 21.

13. A reagent for introducing a gene into a cell, which comprises a composition comprising a cationic amino acid type lipid represented by the following formula (I)-1:

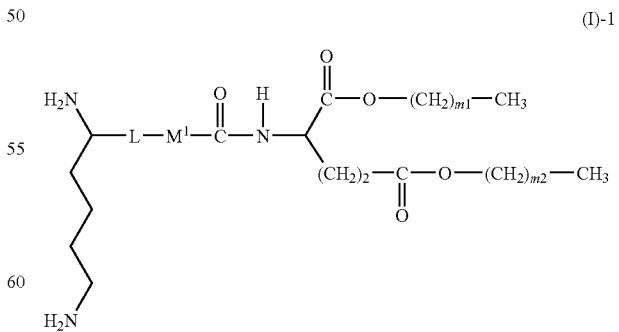

wherein: L is —CONH—, or —S—S—; $M^1$ is —$(CH_2)_k$— or —$(CH_2CH_2O)_k$—; k is an integer between 2 and 14; and m1 and m2 are each independently an integer between 11 and 21; with the proviso that both m1 and m2 are not an integer of 15.

14. The reagent according to claim 12 or 13, wherein the composition further comprises at least one substance selected from the group consisting of diacylphosphatidylcholine, cholesterol, and an amphipathic molecule to which a polyethylene glycol chain is bound.

15. The reagent according to claim 14, wherein one or two acyl chains of diacylphosphatidylcholine is an oleoyl group.

16. The reagent according to claim 12 or 13, wherein the composition is a molecular assembly dispersed in an aqueous medium.

17. The reagent according to claim 16, wherein the molecular assembly forms a bilayer membrane vesicle structure, and wherein an inner aqueous phase thereof includes a protein or gene.

18. The reagent according to claim 12 or 13, wherein the composition is a dry powder product.

19. The reagent according to claim 18, wherein the dry powder product can form a bilayer membrane vesicle structure including a protein or gene when dispersed in an aqueous medium.

20. The reagent according to claim 12 or 13, wherein the cell is: a cell constituting a part of body tissue; plasma, serum or blood; or a cell cultured in a medium containing a part of components thereof.

21. A kit for introducing a protein or gene into a cell, which comprises the reagent according to claim 12 or 13.

22. The reagent according to claim 1, wherein k is an integer between 3 and 5.

23. The reagent according to claim 2, wherein k is an integer between 3 and 5.

* * * * *